US010542226B2

(12) United States Patent
Tanaka et al.

(10) Patent No.: US 10,542,226 B2
(45) Date of Patent: Jan. 21, 2020

(54) IMAGING ELEMENT, ENDOSCOPE, AND ENDOSCOPE SYSTEM

(71) Applicant: OLYMPUS CORPORATION, Tokyo (JP)

(72) Inventors: Takanori Tanaka, Hachioji (JP); Masashi Saito, Akishima (JP); Takatoshi Igarashi, Hachioji (JP); Satoru Adachi, Tsuchiura (JP); Katsumi Hosogai, Tsukuba (JP); Nana Akahane, Yamanashi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/152,629

(22) Filed: Oct. 5, 2018

(65) Prior Publication Data

US 2019/0037155 A1    Jan. 31, 2019

Related U.S. Application Data

(63) Continuation of application No. PCT/JP2017/006604, filed on Feb. 22, 2017.

(30) Foreign Application Priority Data

Apr. 25, 2016    (JP) .................................. 2016-087249

(51) Int. Cl.
*H04N 5/345* (2011.01)
*H04N 5/369* (2011.01)
(Continued)

(52) U.S. Cl.
CPC ....... *H04N 5/3452* (2013.01); *A61B 1/00009* (2013.01); *A61B 1/045* (2013.01);
(Continued)

(58) Field of Classification Search
CPC .... H04N 5/3452; H04N 5/378; H04N 5/3765; H04N 5/3698; H04N 5/3696;
(Continued)

(56) References Cited

U.S. PATENT DOCUMENTS 7,393,321 B2 *    7/2008    Doguchi ............ A61B 1/00009
                                                                 348/70
2010/0238331 A1    9/2010    Umebayashi et al.
(Continued)

FOREIGN PATENT DOCUMENTS

JP    H09-046566 A    2/1997
JP    2008-270650 A    11/2008
(Continued)

OTHER PUBLICATIONS

International Search Report dated Apr. 4, 2017 issued in PCT/JP2017/006604.

*Primary Examiner* — Padma Haliyur
(74) *Attorney, Agent, or Firm* — Scully, Scott, Murphy & Presser, P.C.

(57) ABSTRACT

An imaging element includes: a pixel chip where a pixel unit and a vertical selecting unit are arranged, the pixel unit including plural pixels that are arranged in a two-dimensional matrix, the pixels being configured to generate and output imaging signals; a transmission chip where at least a power source unit and a transmission unit are arranged; plural capacitative chips, each capacitative chip having capacitance functioning as a bypass condenser for a power source in the power source unit; and plural connecting portions configured to electrically connect the pixel chip, the transmission chip, and the capacitative chip respectively to another chip. The transmission chip is layered and connected at a back surface side of the pixel chip. The capacitative chips are layered and connected at a back surface side of the
(Continued)

transmission chip. The connecting portions are arranged so as to overlap one another.

11 Claims, 48 Drawing Sheets

(51) Int. Cl.
  *H04N 5/378* (2011.01)
  *A61B 1/00* (2006.01)
  *A61B 1/045* (2006.01)
  *A61B 1/05* (2006.01)
  *H01L 27/146* (2006.01)
  *H04N 5/376* (2011.01)

(52) U.S. Cl.
  CPC ............ *A61B 1/05* (2013.01); *H01L 27/1469* (2013.01); *H01L 27/14618* (2013.01); *H01L 27/14634* (2013.01); *H01L 27/14636* (2013.01); *H04N 5/3696* (2013.01); *H04N 5/3698* (2013.01); *H04N 5/378* (2013.01); *H04N 5/3765* (2013.01)

(58) Field of Classification Search
  CPC ................ H04N 5/369; H01L 27/1469; H01L 27/14636; H01L 27/14634; H01L 27/14618; H01L 27/14; A61B 1/05; A61B 1/045; A61B 1/00009; A61B 1/04; G02B 23/24
  See application file for complete search history.

(56) References Cited

U.S. PATENT DOCUMENTS

| | | | |
|---|---|---|---|
| 2014/0092216 A1 | 4/2014 | Kawata et al. | |
| 2015/0109505 A1* | 4/2015 | Sakuragi | H04N 5/3575 |
| | | | 348/302 |
| 2015/0189213 A1* | 7/2015 | Tanaka | H04N 5/369 |
| | | | 250/208.1 |
| 2015/0326241 A1* | 11/2015 | Tanaka | H04N 5/378 |
| | | | 250/208.1 |
| 2015/0365567 A1 | 12/2015 | Umebayashi et al. | |
| 2016/0037029 A1* | 2/2016 | Igarashi | G02B 23/2476 |
| | | | 348/65 |
| 2016/0057370 A1* | 2/2016 | Tanaka | H01L 27/14636 |
| | | | 348/302 |
| 2016/0218134 A1 | 7/2016 | Umebayashi et al. | |
| 2016/0233264 A1 | 8/2016 | Kagawa et al. | |
| 2016/0254299 A1 | 9/2016 | Gomi | |
| 2017/0092681 A1 | 3/2017 | Umebayashi et al. | |
| 2017/0100020 A1* | 4/2017 | Ochi | A61B 1/015 |
| 2018/0012924 A1 | 1/2018 | Umebayashi et al. | |
| 2018/0076249 A1 | 3/2018 | Umebayashi et al. | |

FOREIGN PATENT DOCUMENTS

| | | |
|---|---|---|
| JP | 2011-050496 A | 3/2011 |
| JP | 2014-017834 A | 1/2014 |
| JP | 2015-065479 A | 4/2015 |
| JP | 2015-115420 A | 6/2015 |
| WO | WO 2013/176055 A1 | 11/2013 |
| WO | WO 2015/050000 A1 | 4/2015 |
| WO | WO 2016/006302 A1 | 1/2016 |

* cited by examiner

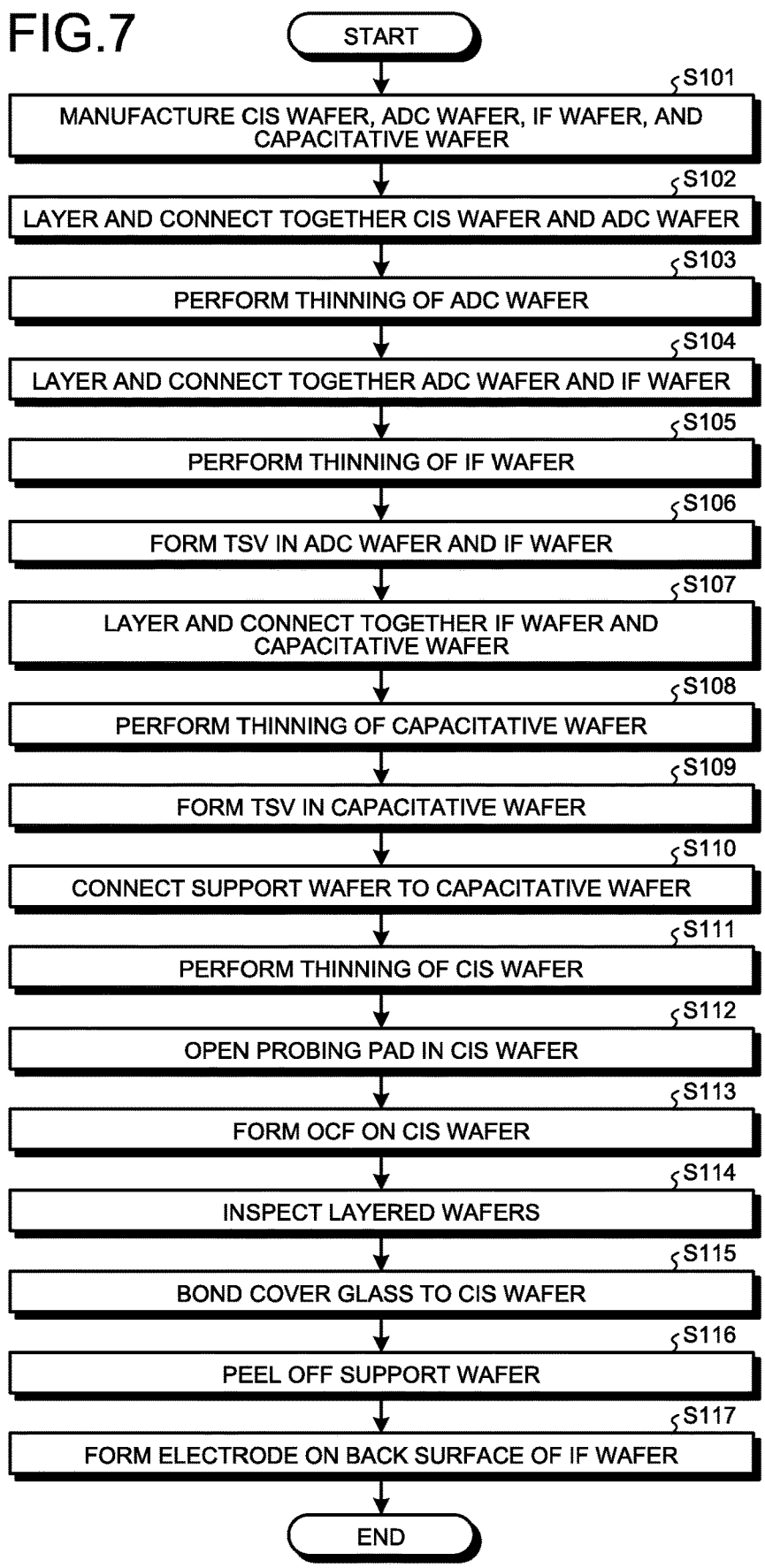

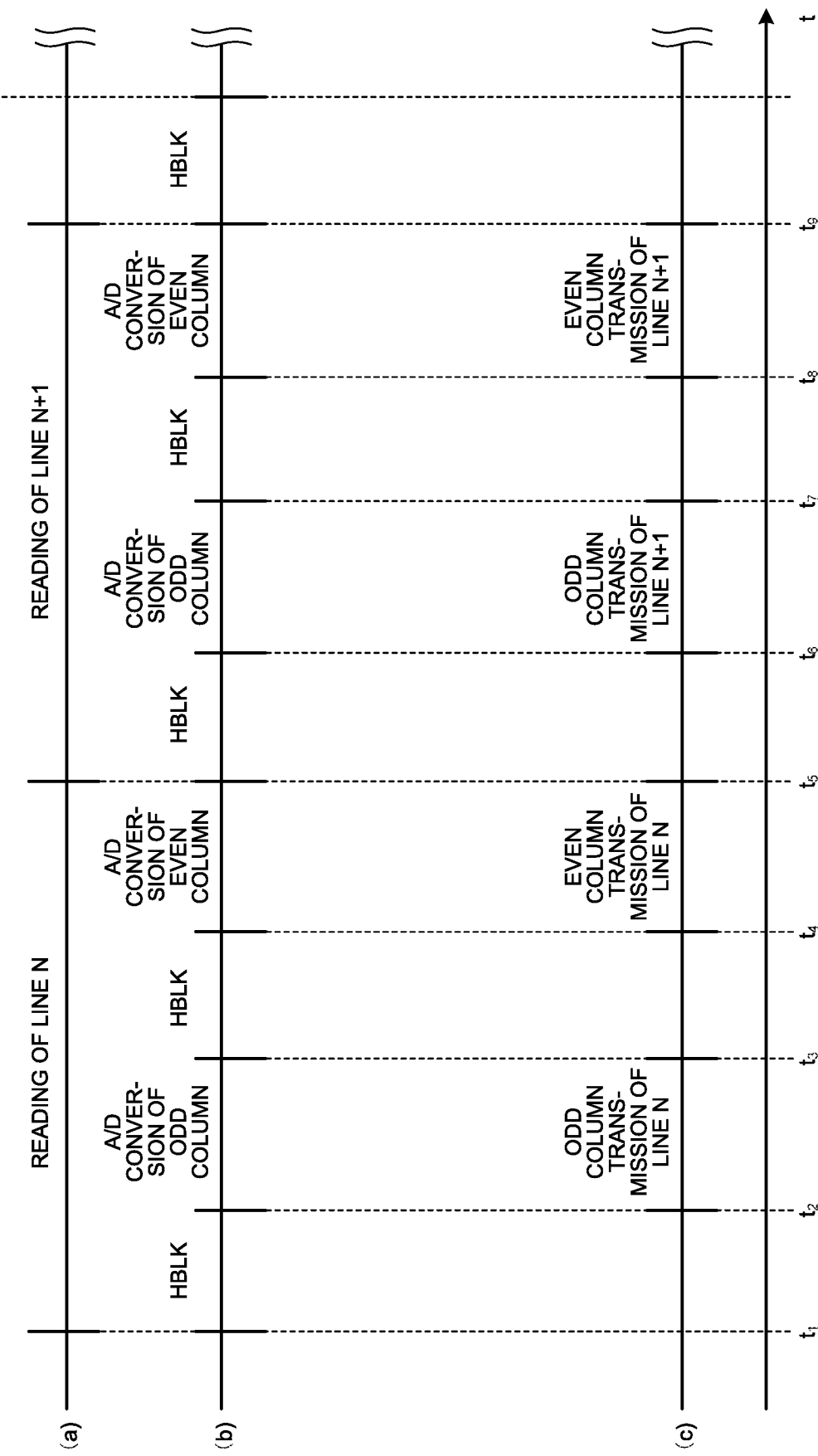

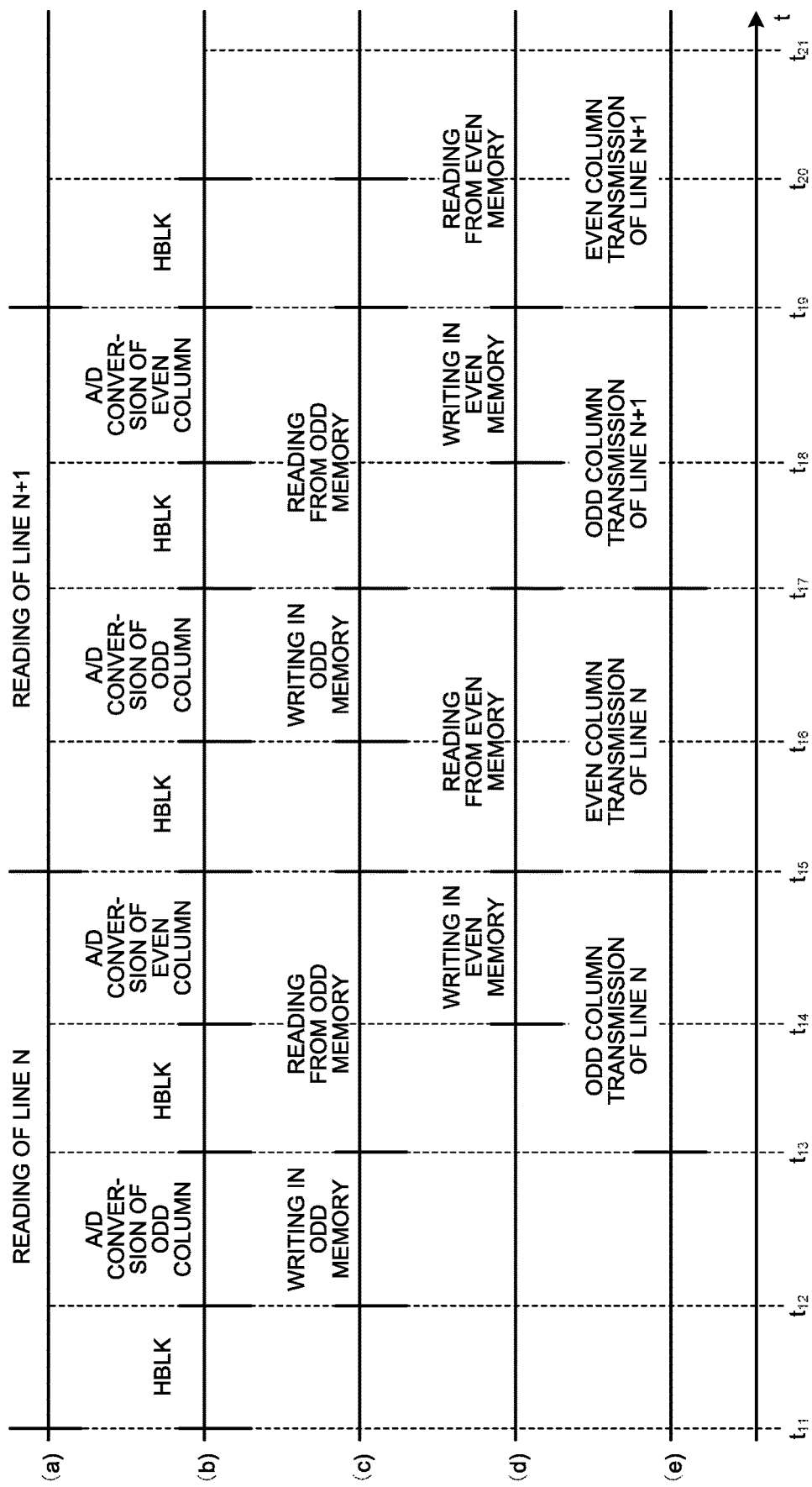

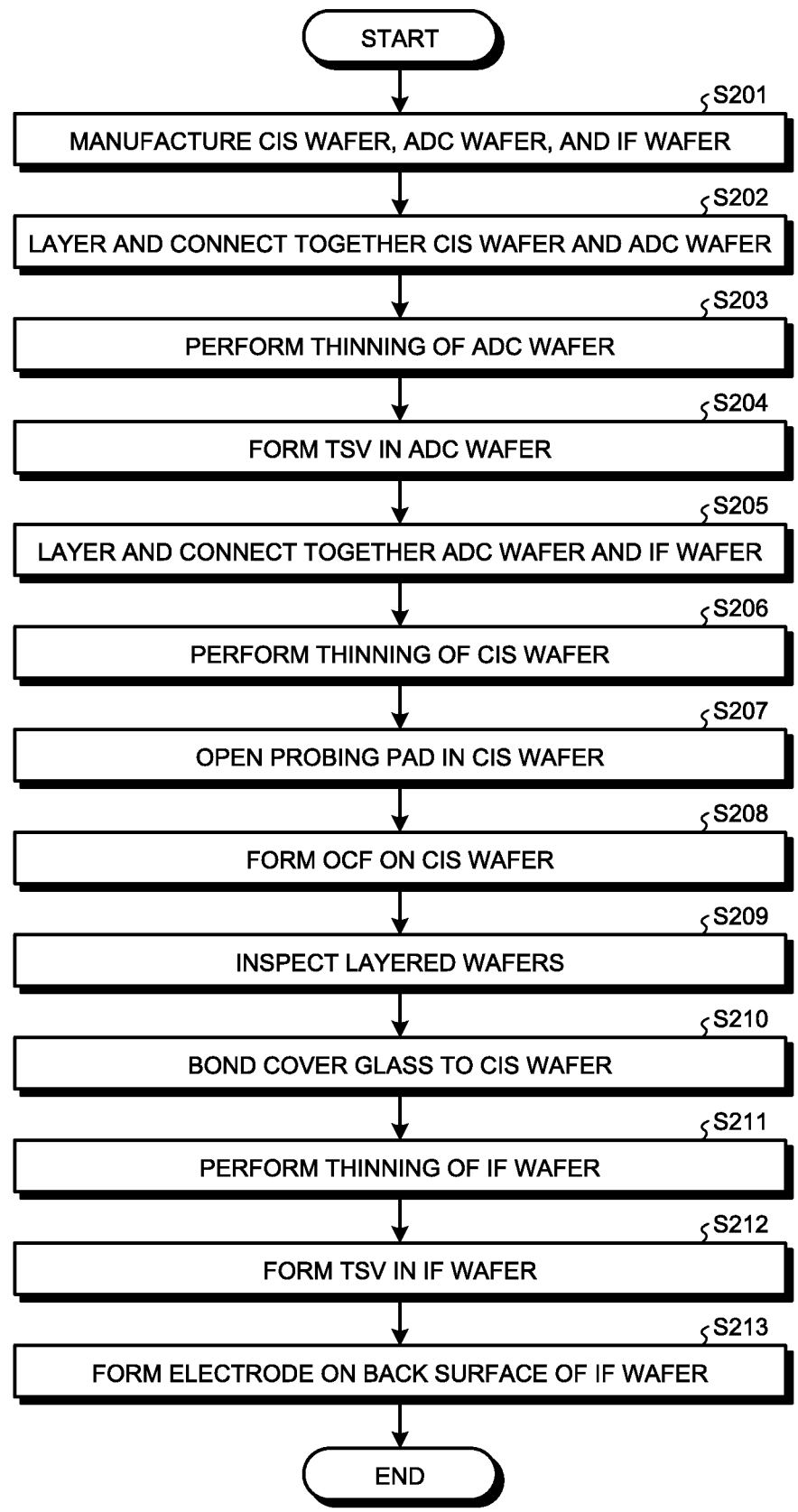

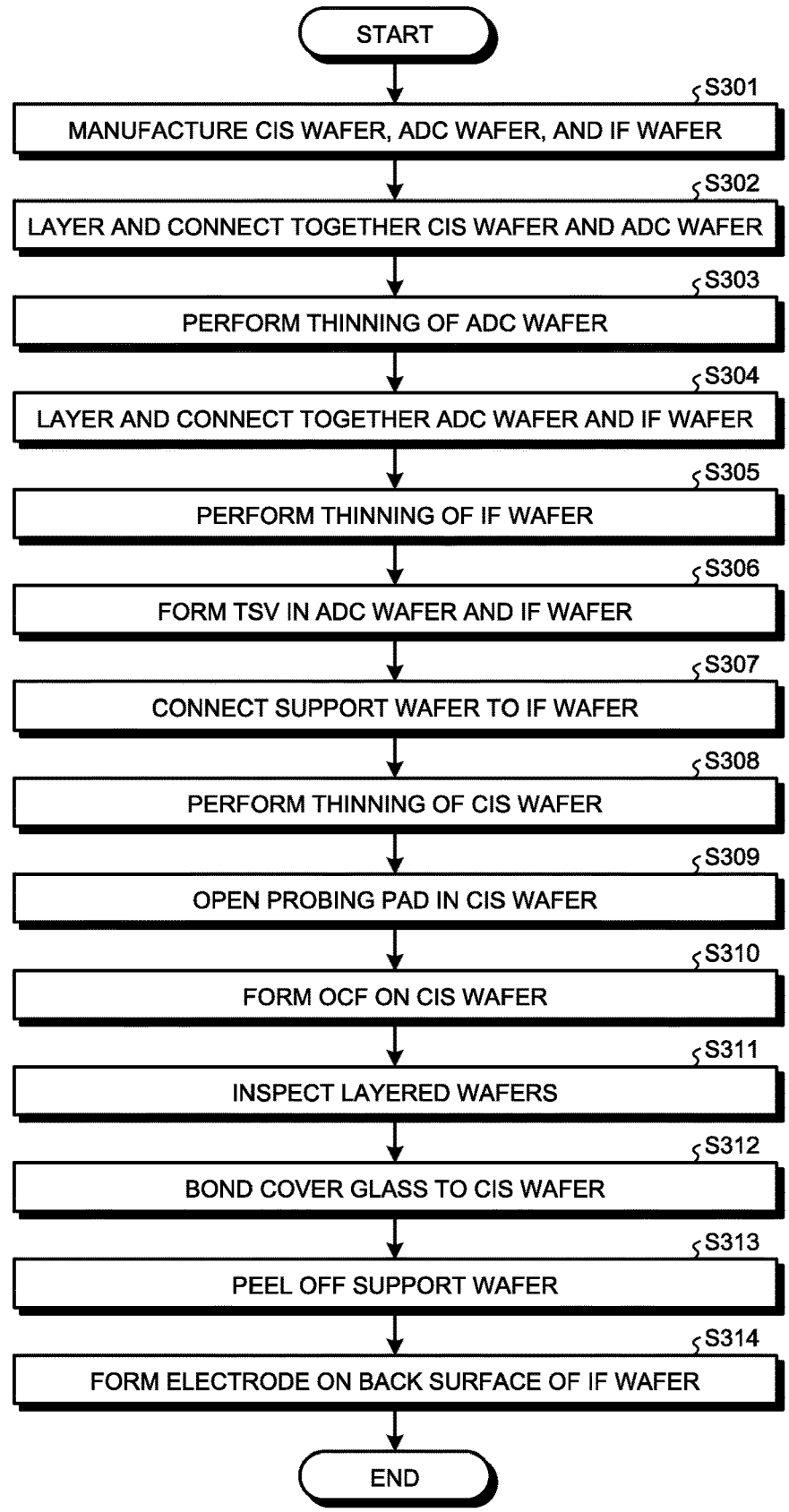

IMAGING ELEMENT, ENDOSCOPE, AND ENDOSCOPE SYSTEM

CROSS REFERENCES TO RELATED APPLICATIONS

This application is a continuation of PCT international application Ser. No. PCT/JP2017/006604 filed on Feb. 22, 2017 which designates the United States, incorporated herein by reference, and which claims the benefit of priority from Japanese Patent Applications No. 2016-087249, filed on Apr. 25, 2016, incorporated herein by reference.

BACKGROUND

1. Technical Field

The present disclosure relates to an imaging element, an endoscope, and an endoscope system, for imaging a subject and generating image data of the subject.

2. Related Art

In the related art, an imaging signal captured by an imaging element provided at a distal end of an insertion unit inserted in a body cavity needs to be transmitted from an endoscope to an image processing apparatus via a cable. When the imaging signal is transmitted via the cable as an analog signal as is, there is a limit to the pixel rate, and it is difficult to improve the image quality by increase in the number of pixels of the imaging element. Therefore, the imaging element for the endoscope needs to include an A/D conversion circuit that A/D-converts the analog imaging signal to a digital imaging signal.

For example, disclosed in Japanese Patent Application Laid-open No. 2014-017834 is a parallel column AD conversion circuit having a peripheral circuit arranged on a different chip for reduction of the chip area. According to this technique, the chip having the pixel area and the chip having the peripheral circuit are layered over each other, and these chips are connected via a through-silicon via (TSV) or the like.

SUMMARY

In some embodiments, an imaging element includes: a pixel chip where a pixel unit and a vertical selecting unit are arranged, the pixel unit including plural pixels that are arranged in a two-dimensional matrix, the pixels being configured to generate and output imaging signals according to quantity of received light, the vertical selecting unit being configured to sequentially select the pixel unit in row units and read out the imaging signals; a transmission chip where at least a power source unit and a transmission unit configured to transmit the imaging signals to a transmission cable are arranged; plural capacitative chips, each capacitative chip having capacitance functioning as a bypass condenser for a power source in the power source unit; and plural connecting portions configured to electrically connect the pixel chip, the transmission chip, and the capacitative chip respectively to another chip. The transmission chip is layered and connected, along a direction orthogonal to a light receiving surface of the pixel unit, at a back surface side of the pixel chip relative to a light entering surface of the pixel chip, by the connecting portions, the capacitative chips are layered and connected, along the direction orthogonal to the light receiving surface of the pixel unit, at a back surface side of the transmission chip relative to a surface of the transmission chip, the surface being where the pixel chip has been layered, and the connecting portions are arranged so as to overlap one another as viewed in the direction orthogonal to the light receiving surface of the pixel unit.

In some embodiments, an endoscope includes: the imaging element at a distal end of an insertion unit of the endoscope, the insertion unit being insertable in a subject.

In some embodiments, an endoscope system includes: the endoscope; and an image processing apparatus configured to convert the imaging signals into image signals.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 7 is a flow chart illustrating an outline of a manufacturing method for the imaging element according to the first embodiment of the disclosure;

FIG. 9 is a timing chart illustrating operation of the imaging element according to the first embodiment of the disclosure;

FIG. 14 is a timing chart illustrating operation of the imaging element according to the second embodiment of the disclosure;

FIG. 20 is a flow chart illustrating an outline of a manufacturing method for the imaging element according to the fifth embodiment of the disclosure;

FIG. 22 is a flow chart illustrating an outline of a manufacturing method for an imaging element according to a first modified example of the fifth embodiment of the disclosure;

DETAILED DESCRIPTION

Hereinafter, as modes for implementation of the disclosure (hereinafter, referred to as "embodiments"), endoscope systems, each of which includes an endoscope having an imaging element provided at a distal end of an insertion unit to be inserted in a subject, will be described. Further, the disclosure is not limited to these embodiments. Furthermore, description will be made with the same reference signs each being assigned to portions that are the same, throughout the drawings. Moreover, the drawings are schematic, and it needs to be noted that a relation between a thickness and a width of each member and ratios among the members may be different from the actual relation and ratios. In addition, there may be portions that differ in their dimensions and ratios among the drawings, too.

First Embodiment

Configuration of Endoscope System

Figure 1:
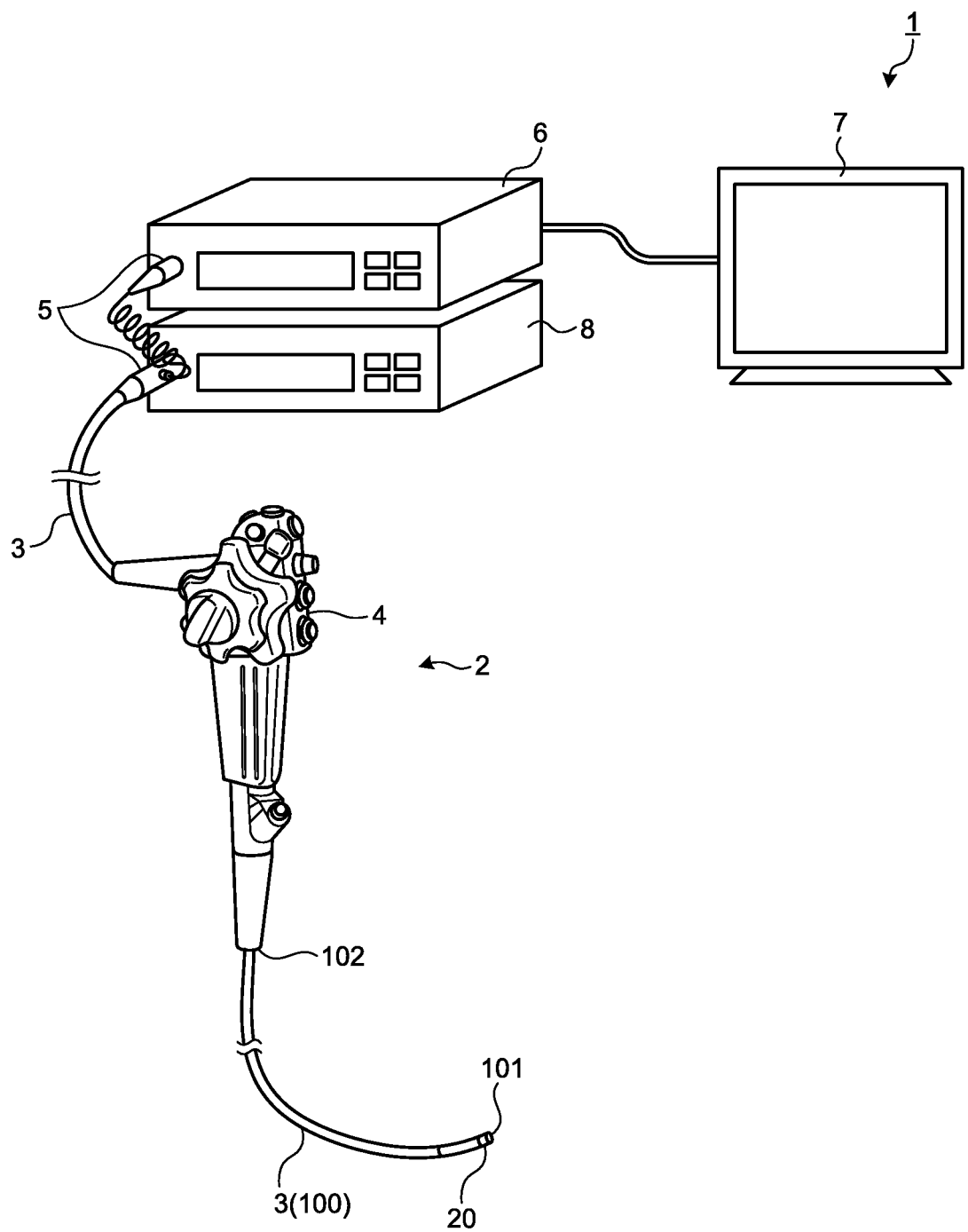
FIG. 1 is a schematic diagram schematically illustrating the overall configuration of an endoscope system according to a first embodiment of the disclosure.

FIG. 1 is a schematic diagram schematically illustrating an overall configuration of an endoscope system according to a first embodiment of the disclosure. An endoscope system 1 illustrated in FIG. 1 includes an endoscope 2, a transmission cable 3, a connector unit 5, a processor 6 (an image processing apparatus), a display device 7, and a light source device 8.

In the endoscope 2, by insertion of an insertion unit 100, which is a part of the transmission cable 3, into a body cavity of a subject, an in-vivo image of the subject is captured and an imaging signal (image data) is output to the processor 6. In the endoscope 2, an imaging element 20 (an imaging device), which captures the in-vivo image, is provided at a distal end 101 of the insertion unit 100 to be inserted in the body cavity of the subject, the distal end 101 being at one end of the transmission cable 3. Further, in the endoscope 2, an operating unit 4, which receives various operations for the endoscope 2, is provided at a proximal end 102 of the insertion unit 100. The imaging signal of the image captured by the imaging element 20, for example, passes through the transmission cable 3 having a length of a few meters, and is output to the connector unit 5.

The transmission cable 3 connects between the endoscope 2 and the connector unit 5, and connects between the endoscope 2 and the light source device 8. Further, the transmission cable 3 propagates therethrough the imaging signal generated by the imaging element 20, to the connector unit 5. The transmission cable 3 is configured by use of a cable, an optical fiber, or the like.

The connector unit 5 is connected to the endoscope 2, the processor 6, and the light source device 8, performs predetermined signal processing on the imaging signal output by the endoscope 2 connected thereto, and outputs the signal-processed imaging signal to the processor 6.

The processor 6 performs predetermined image processing on the imaging signal input from the connector unit 5, and outputs the image-processed imaging signal to the display device 7. The processor 6 integrally controls the whole endoscope system 1. For example, the processor 6 performs control of changing illumination light emitted by the light source device 8 and changing the imaging mode of the endoscope 2.

The display device 7 displays thereon an image corresponding to the imaging signal that has been image-processed by the processor 6. Further, the display device 7 displays thereon various types of information related to the endoscope system 1. The display device 7 is configured by use of a display panel or the like, of liquid crystal, organic electroluminescence, or the like.

The light source device 8 emits illumination light to the subject from the distal end 101 of the insertion unit 100 of the endoscope 2, via the connector unit 5 and the transmission cable 3. The light source device 8 is configured by use of a white light emitting diode (LED) that emits white light, an LED that emits special light of narrow band light having a wavelength bandwidth narrower than a wavelength bandwidth of the white light, and the like. The light source device 8 emits the white light or narrow band light to the subject via the endoscope 2, under control by the processor 6. In this first embodiment, the light source device 8 is described as that of the simultaneous type, but the light source device 8 may be that of the field sequential type that sequentially emits red, green, and blue light.

Figure 2:
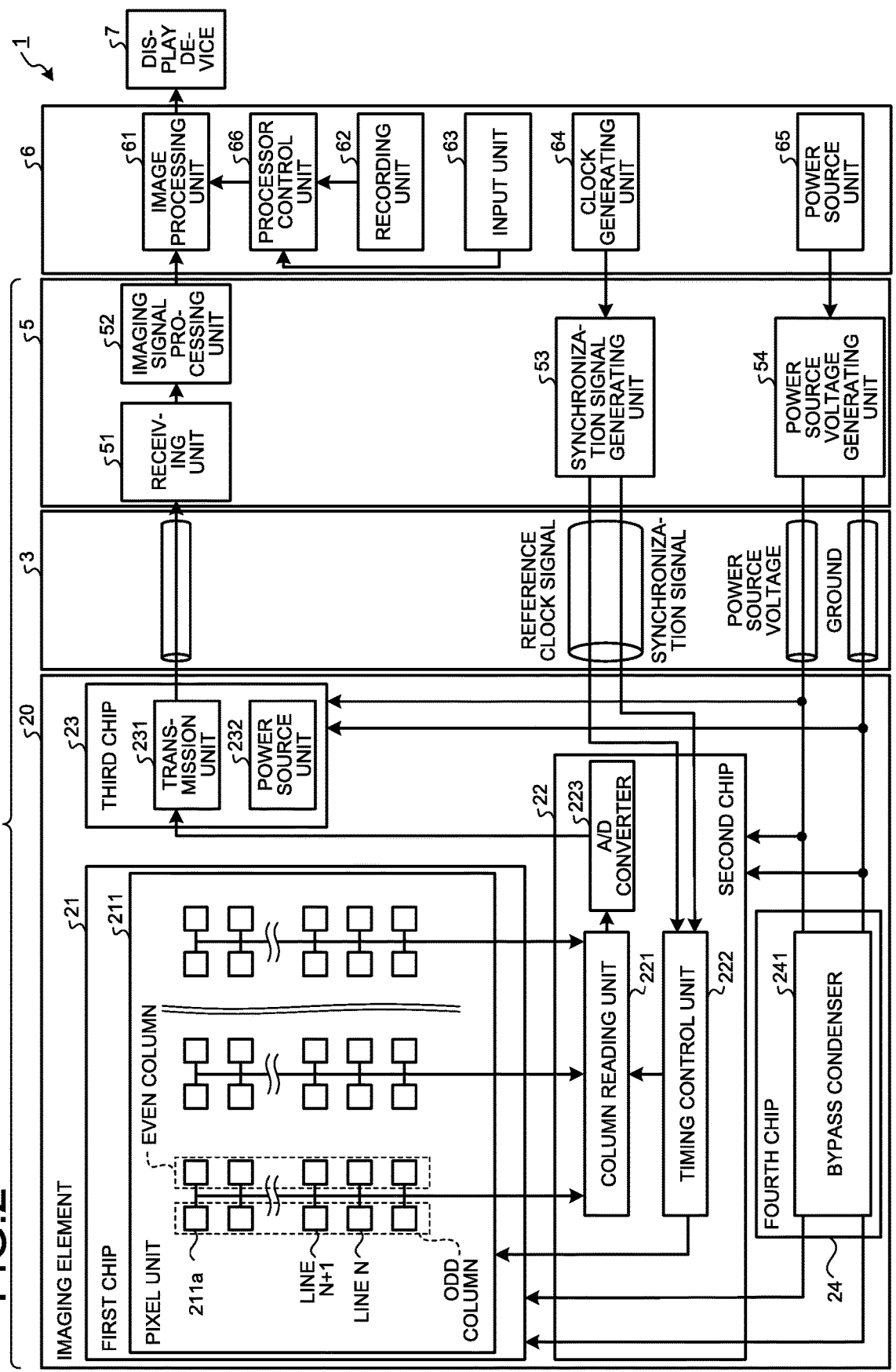
FIG. 2 is a block diagram illustrating functions of main parts of the endoscope system according to the first embodiment of the disclosure.

FIG. 2 is a block diagram illustrating functions of main parts of the endoscope system 1. By reference to FIG. 2, details of a configuration of each part of the endoscope system 1 and paths of electric signals in the endoscope system 1 will be described.

Configuration of Endoscope

Firstly, a configuration of the endoscope 2 will be described. The endoscope 2 includes the imaging element 20, the transmission cable 3, and the connector unit 5.

The imaging element 20 includes a first chip 21, a second chip 22, a third chip 23, and a fourth chip 24. The first chip 21, the second chip 22, the third chip 23, and the fourth chip 24 are layered over and connected to one another. Further, the imaging element 20 receives, via the transmission cable 3, power source voltage VDD generated by a later described power source voltage generating unit 54 of the connector unit 5, together with a ground GND.

The first chip 21 is realized by use of a complementary metal oxide semiconductor (CMOS) image sensor (CIS) chip. Specifically, the first chip 21 includes a pixel unit 211 (a light receiving unit) formed of plural pixels 211a arranged therein, which are arranged in a two-dimensional matrix, receive light from outside, and generate and output imaging signals according to quantity of the light received.

The pixel unit 211 is realized by use of a photoelectric conversion element (a photodiode), a transfer transistor, a charge-voltage conversion transistor, a pixel output transistor, and the like. Hereinafter, an example where the pixel unit 211 is of the two sharing pixel type that reads out two pixels 211a with one vertical transfer line will be described; but not being limited to this example, for example, the pixel unit 211 may be of: the four sharing pixel type that reads out four pixels 211a with one vertical transfer line; the eight sharing pixel type that reads eight pixels 211a with one vertical transfer line; or the type that reads out one pixel 211a with one vertical transfer line.

The second chip 22 is realized by use of an analog-to-digital converter (ADC) chip. The second chip 22 includes a column reading unit 221, a timing control unit 222, and an A/D converter 223.

Based on a signal input from the timing control unit 222, the column reading unit 221 sequentially selects predetermined pixels from the plural pixels 211a in the pixel unit 211, reads out imaging signals from the selected pixels, and outputs the imaging signals to the A/D converter 223.

Based on a reference clock signal and a synchronization signal input from the connector unit 5, the timing control unit 222 generates a timing signal, and outputs this timing signal to the column reading unit 221.

The A/D converter 223 converts the analog imaging signal input from the column reading unit 221 into a digital imaging signal, and outputs the digital imaging signal to a transmission unit 231 of the third chip 23 described later.

The third chip 23 is realized by use of an interface (IF) chip. The third chip 23 includes: the transmission unit 231 that performs parallel-serial conversion on the multi-bit digital imaging signal input from the A/D converter 223, and transmits the converted imaging signal to the transmission cable 3 by a differential method; and a power source unit 232 that drives the transmission unit 231.

The fourth chip 24 is realized by use of a capacitative chip. The fourth chip 24 includes a bypass condenser 241, which is provided between the power source voltage VDD and the ground GND that are supplied to the imaging element 20, and which is for power source stabilization. In this first embodiment, the fourth chip functions as the capacitative chip.

The connector unit 5 includes a receiving unit 51, an imaging signal processing unit 52, a synchronization signal generating unit 53, and a power source voltage generating unit 54.

The receiving unit 51 receives the differential imaging signal transmitted from the imaging element 20, performs serial-parallel conversion on the differential imaging signal, and outputs the converted imaging signal to the imaging signal processing unit 52.

The imaging signal processing unit 52 is formed of, for example, a field programmable gate array (FPGA), performs processing, such as noise removal and format conversion processing, on the digital imaging signal input from the receiving unit 51, and outputs the processed imaging signal to the processor 6.

The synchronization signal generating unit 53 generates, based on a reference clock signal (for example, a clock signal of 27 MHz), which is supplied from the processor 6 and serves as a reference for operation of each part forming the endoscope 2, a synchronization signal indicating a start position of each frame, and outputs, together with the reference clock signal, the generated synchronization signal, to the timing control unit 222 of the imaging element 20, via the transmission cable 3. The synchronization signal generated by the synchronization signal generating unit 53 includes a horizontal synchronization signal and a vertical synchronization signal.

The power source voltage generating unit 54 generates, from power supplied from the processor 6, power source voltage needed to drive each of the first chip 21, the second chip 22, the third chip 23, and the fourth chip 24, and outputs the power source voltage to the first chip 21, the second chip 22, the third chip 23, and the fourth chip 24. The power source voltage generating unit 54 generates the power source voltage needed to drive the first chip 21, the second chip 22, the third chip 23, and the fourth chip 24, by using a regulator or the like.

Configuration of Processor

Next, a configuration of the processor 6 will be described. The processor 6 is a control device that integrally controls the whole endoscope system 1. The processor 6 includes an image processing unit 61, a recording unit 62, an input unit 63, a clock generating unit 64, a power source unit 65, and a processor control unit 66.

The image processing unit 61 converts the digital imaging signal that has been signal-processed by the imaging signal processing unit 52, to an image signal by performing image processing, such as synchronization processing, white balance (WB) adjustment processing, gain adjustment processing, gamma correction processing, digital/analog (D/A) conversion processing, and format conversion processing, on the digital imaging signal, and outputs this image signal to the display device 7 (display unit).

The recording unit 62 records therein various types of information related to the endoscope system 1, data being processed, and the like. The recording unit 62 is configured by use of a recording medium, such as a flash memory, or a random access memory (RAM).

The input unit 63 receives input of various operations related to the endoscope system 1. For example, the input unit 63 receives input of an instruction signal for change of the type of the illumination light emitted by the light source device 8. The input unit 63 is configured by use of, for example, a cross switch and push buttons.

The clock generating unit 64 generates a reference clock signal serving as a reference for operation of each part forming the endoscope system 1, and outputs this reference clock signal to the synchronization signal generating unit 53.

The power source unit 65 generates the power source voltage VDD, and supplies the generated power source voltage VDD, together with the ground GND, to the power source voltage generating unit 54 of the connector unit 5.

The processor control unit 66 integrally controls the respective parts forming the endoscope system 1. The processor control unit 66 is configured by use of a central processing unit (CPU) or the like. The processor control unit 66 changes, according to an instruction signal input from the input unit 63, the illumination light emitted by the light source device 8.

Structure of Imaging Unit

Figure 3:
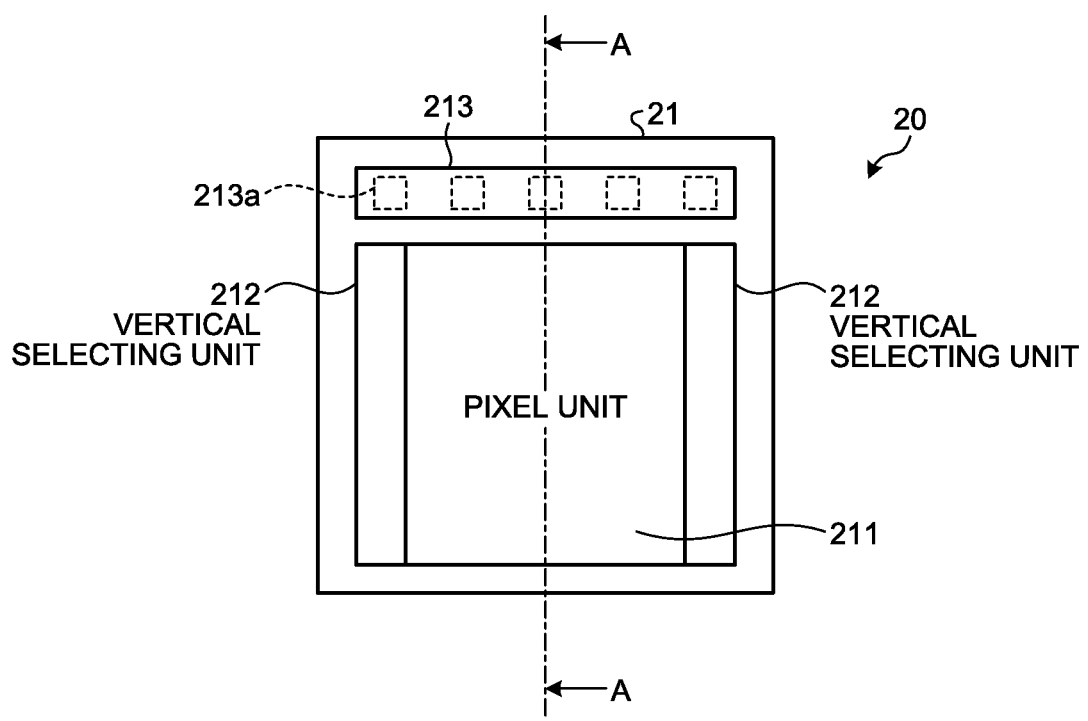
FIG. 3 is a top view of an imaging element according to the first embodiment of the disclosure.
Figure 4:
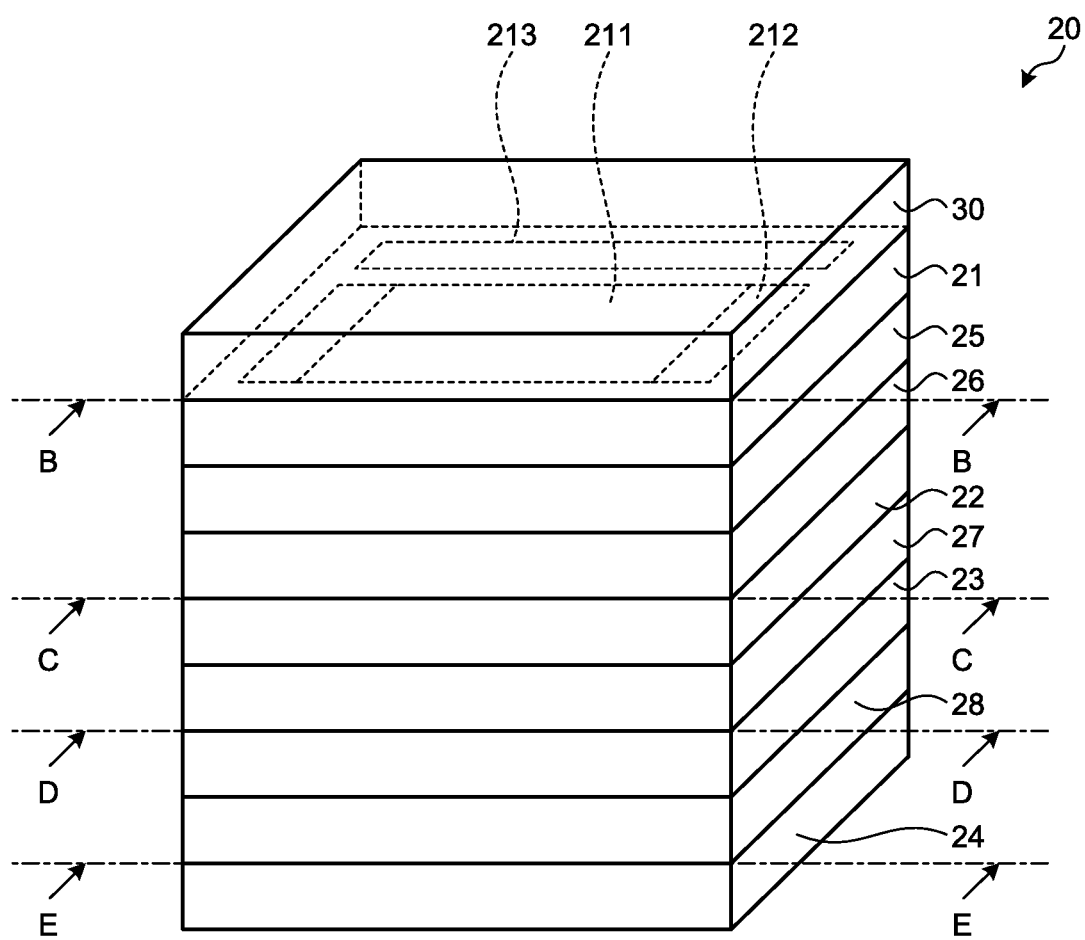
FIG. 4 is a perspective view of the imaging element according to the first embodiment of the disclosure.
Figure 5:
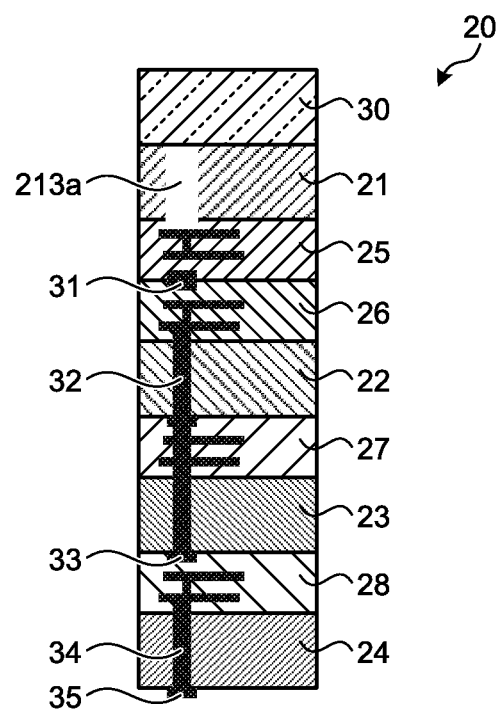
FIG. 5 is a sectional view along a line A-A in FIG. 3.
Figure 6A:
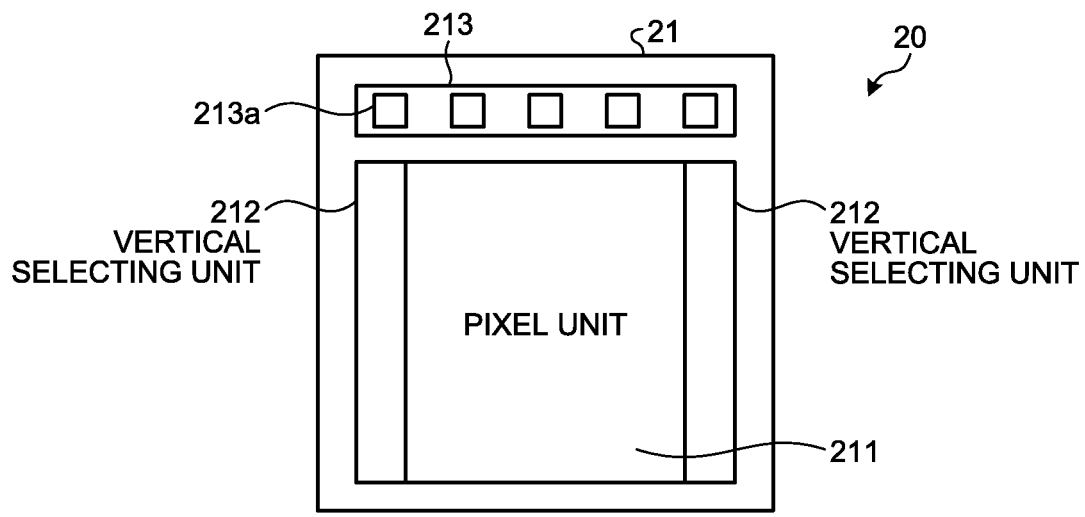
FIG. 6A is a sectional view along a line B-B in FIG. 4.
Figure 6B:
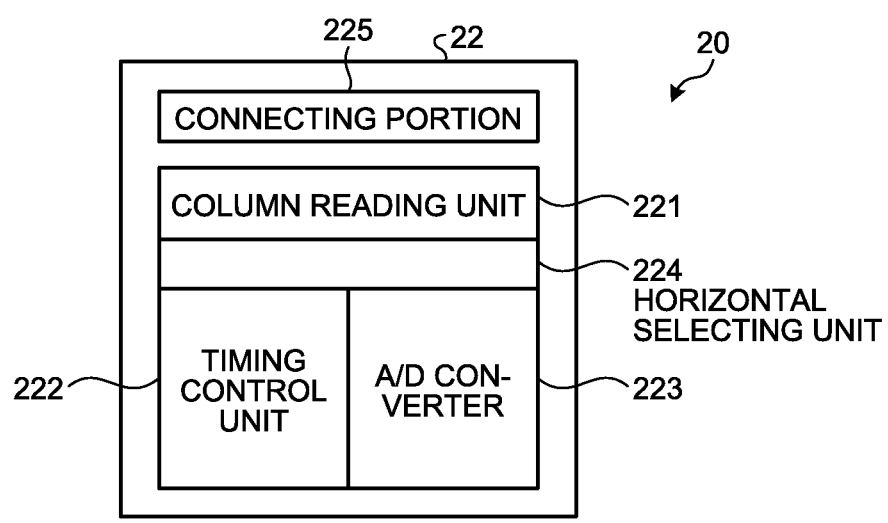
FIG. 6B is a sectional view along a line C-C in FIG. 4.
Figure 6C:
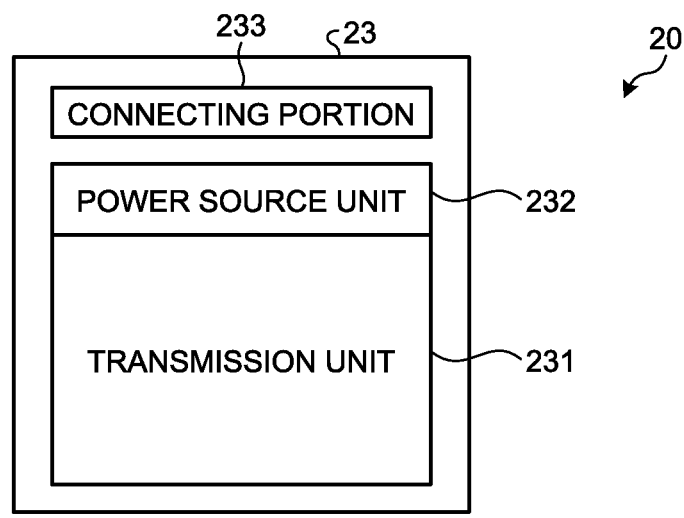
FIG. 6C is a sectional view along a line D-D in FIG. 4.
Figure 6D:
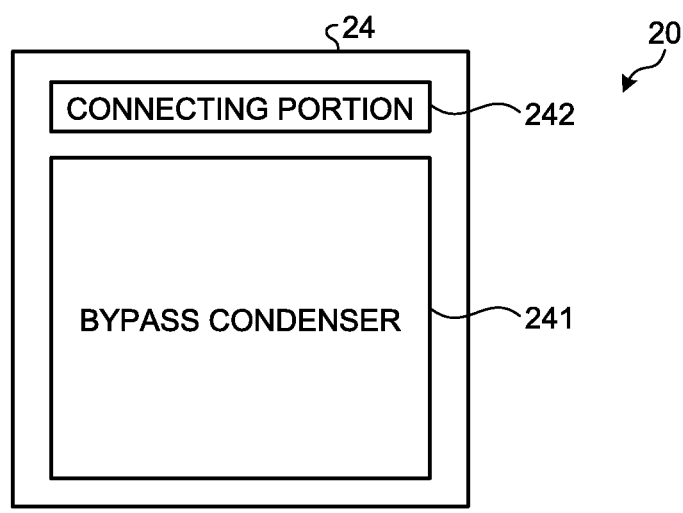
FIG. 6D is a sectional view along a line E-E in FIG. 4.

Next, a detailed structure of the imaging element 20 will be described. FIG. 3 is a top view of the imaging element 20. FIG. 4 is a perspective view of the imaging element 20. FIG. 5 is a sectional view along a line A-A in FIG. 3. FIG. 6A is a sectional view along a line B-B in FIG. 4. FIG. 6B is a sectional view along a line C-C in FIG. 4. FIG. 6C is a sectional view along a line D-D in FIG. 4. FIG. 6D is a sectional view along a line E-E in FIG. 4.

As illustrated in FIG. 3 to FIG. 5 and FIG. 6A to FIG. 6D, the imaging element 20 is formed of the fourth chip 24, a fourth multi-layered wiring layer 28, the third chip 23, a third multi-layered wiring layer 27, the second chip 22, a second multi-layered wiring layer 26, a first multi-layered wiring layer 25, the first chip 21, and a cover glass 30 (a cover glass wafer), which are layered over one another in this order along a direction orthogonal to a plane of the pixel unit 211 on the first chip 21 (an up-down direction on the plane of paper in FIG. 5). Further, the imaging element 20 includes TSVs 32 and 34 formed therein, which electrically connect the respective layers. Furthermore, the imaging element 20 includes a probing pad 213a, which is formed at a light receiving surface side of the first chip 21, and with which an inspection probe for image inspection is to be contacted. Moreover, the imaging element 20 includes electrodes 31, 33, and 35, formed therein, which electrically connect the respective layers.

The first chip 21 includes, as illustrated in FIG. 6A: the pixel unit 211 that is rectangular; a vertical selecting unit 212 (a vertical selecting circuit) that is provided at both a left end and a right end of the pixel unit 211, sequentially selects imaging signals from the respective pixels 211a in the pixel unit 211 in row units, and causes vertical transfer lines (not illustrated in the drawings) to transfer the imaging signals; a connecting portion 213 that is arranged at an upper end of the pixel unit 211, connects to the second chip 22, and is rectangular; and the probing pad 213a that is provided in the connecting portion 213. Further, the probing pad 213a is formed in the first chip 21, so as to overlap the connecting portion 213 as viewed from the light receiving surface side of the pixel unit 211.

The second chip 22 includes, as illustrated in FIG. 6B, the column reading unit 221 (column reading circuit), the timing control unit 222, the A/D converter 223, a horizontal selecting unit 224 (a horizontal selecting circuit) that selects the column reading unit 221 and causes an imaging signal to be transferred, and a connecting portion 225. The connecting portion 225 is arranged on an upper end side of the column reading unit 221.

The third chip 23 includes, as illustrated in FIG. 6C, the transmission unit 231 (cable transmission circuit), the power source unit 232, and a connecting portion 233. The connecting portion 233 is arranged on an upper end side of the power source unit 232.

The fourth chip 24 includes, as illustrated in FIG. 6D, the bypass condenser 241, and a connecting portion 242. The connecting portion 242 is arranged on an upper end side of the bypass condenser 241.

In the imaging element 20 configured as described above, the connecting portion 213, the connecting portion 225, the connecting portion 233, and the connecting portion 242 are respectively arranged on the chips so as to overlap one another as viewed in a direction orthogonal to the light receiving surface of the pixel unit 211. Thereby, the area of each chip is able to be reduced, and thus the imaging element 20 is able to be downsized.

Manufacturing Method for Imaging Unit

Figure 8A:
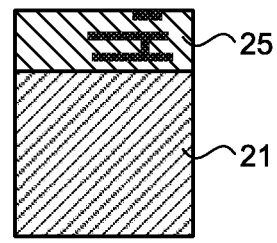
FIG. 8A is a schematic diagram illustrating a cross section of the imaging element at a manufacturing step in FIG. 7.
Figure 8B:
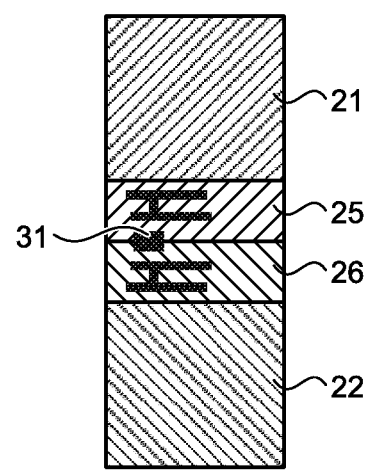
FIG. 8B is a schematic diagram illustrating a cross section of the imaging element at a manufacturing step in FIG. 7.
Figure 8C:
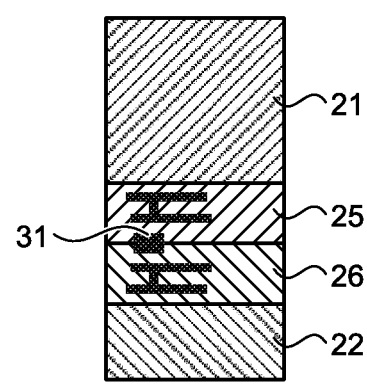
FIG. 8C is a schematic diagram illustrating a cross section of the imaging element at a manufacturing step in FIG. 7.
Figure 8D:
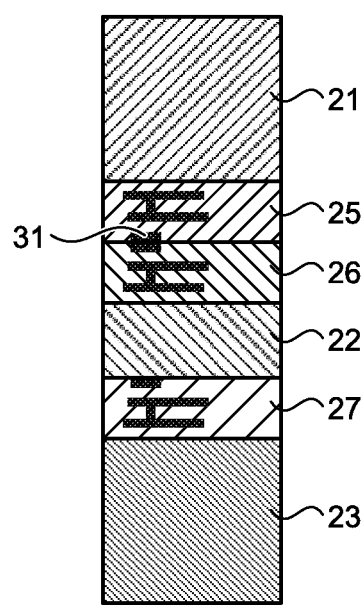
FIG. 8D is a schematic diagram illustrating a cross section of the imaging element at a manufacturing step in FIG. 7.
Figure 8E:
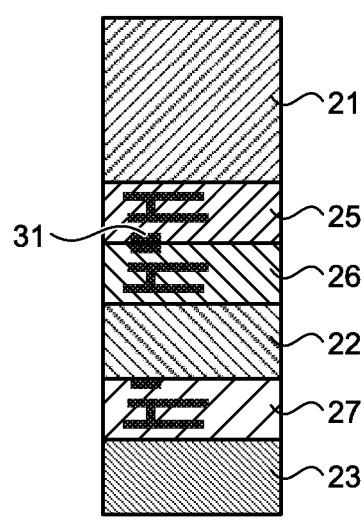
FIG. 8E is a schematic diagram illustrating a cross section of the imaging element at a manufacturing step in FIG. 7.
Figure 8F:
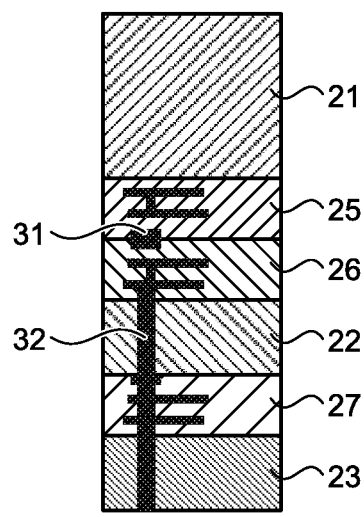
FIG. 8F is a schematic diagram illustrating a cross section of the imaging element at a manufacturing step in FIG. 7.
Figure 8G:
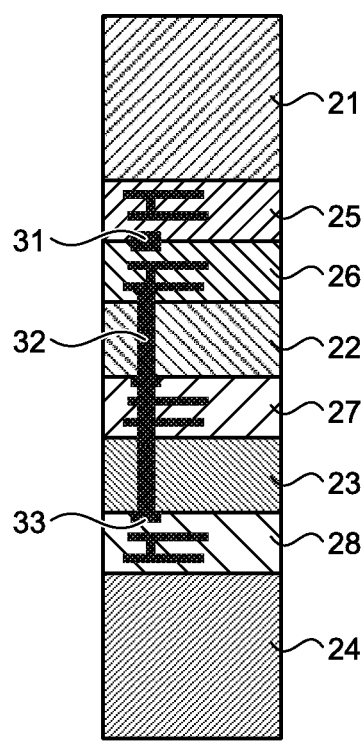
FIG. 8G is a schematic diagram illustrating a cross section of the imaging element at a manufacturing step in FIG. 7.
Figure 8H:
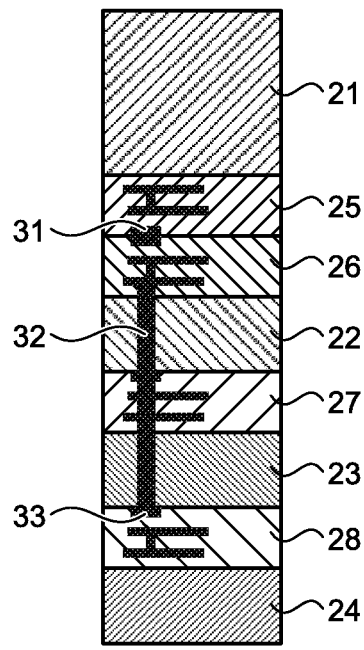
FIG. 8H is a schematic diagram illustrating a cross section of the imaging element at a manufacturing step in FIG. 7.
Figure 8I:
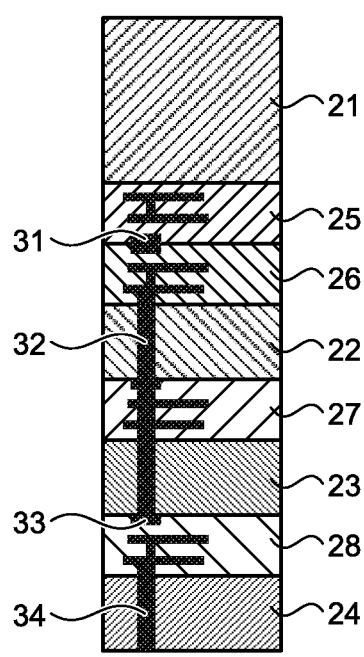
FIG. 8I is a schematic diagram illustrating a cross section of the imaging element at a manufacturing step in FIG. 7.
Figure 8J:
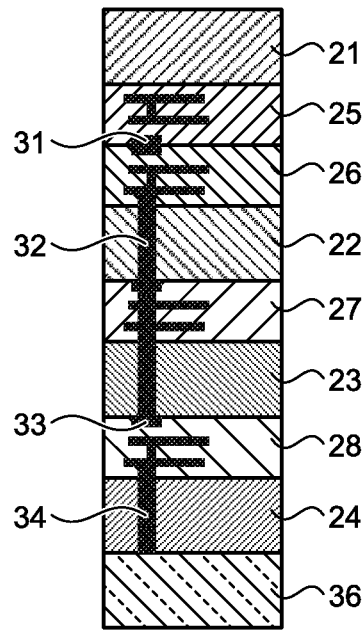
FIG. 8J is a schematic diagram illustrating a cross section of the imaging element at a manufacturing step in FIG. 7.
Figure 8K:
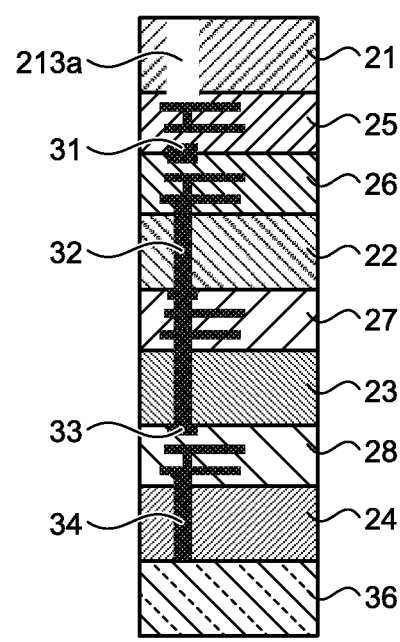
FIG. 8K is a schematic diagram illustrating a cross section of the imaging element at a manufacturing step in FIG. 7.
Figure 8L:
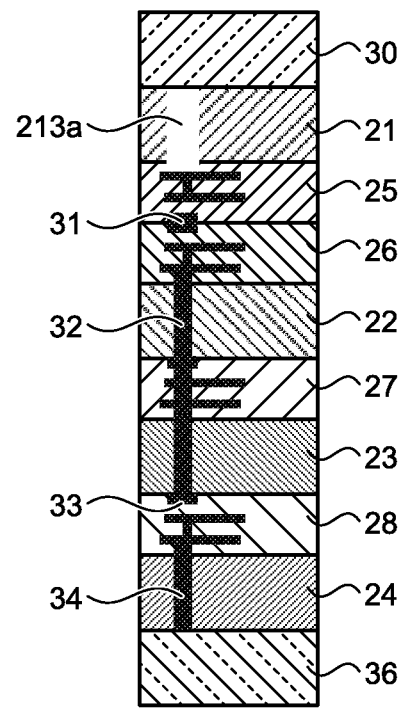
FIG. 8L is a schematic diagram illustrating a cross section of the imaging element at a manufacturing step in FIG. 7.
Figure 8M:
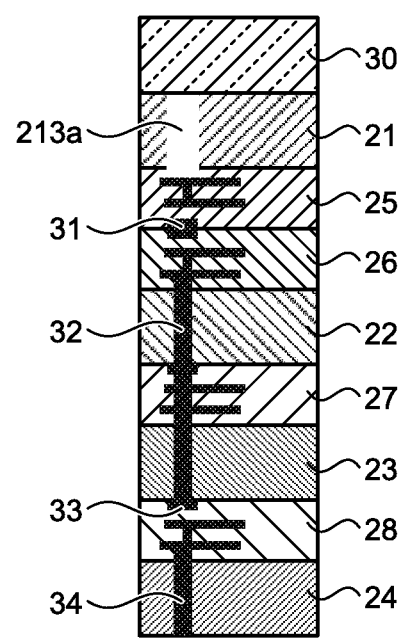
FIG. 8M is a schematic diagram illustrating a cross section of the imaging element at a manufacturing step in FIG. 7.
Figure 8N:
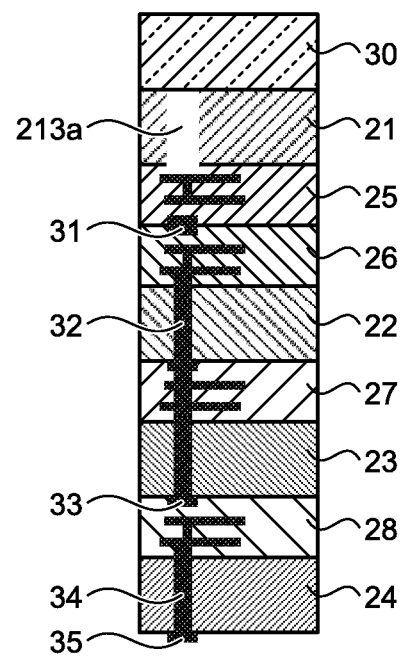
FIG. 8N is a schematic diagram illustrating a cross section of the imaging element at a manufacturing step in FIG. 7.
Figure 10A:
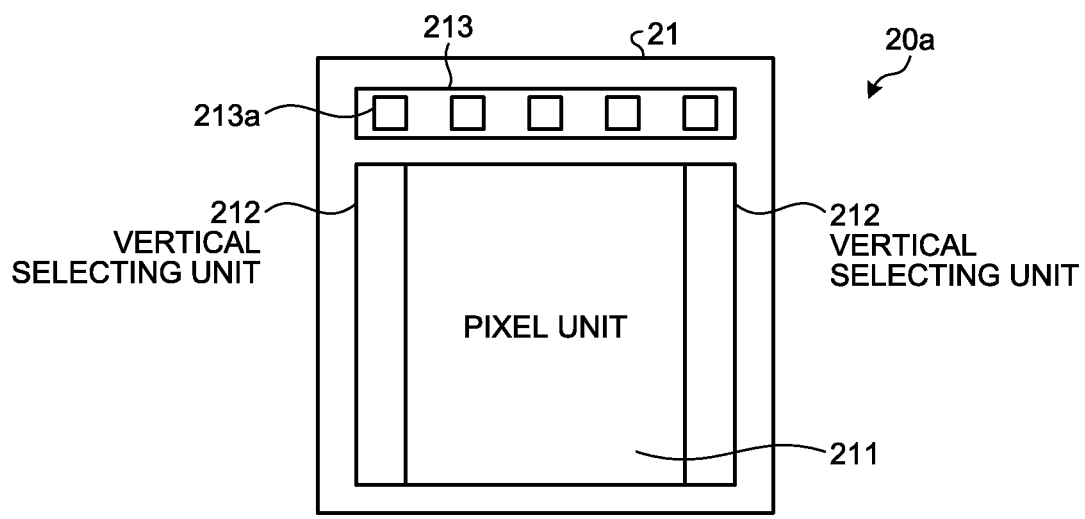
FIG. 10A is a plan view schematically illustrating a first chip forming an imaging element according to a modified example of the first embodiment of the disclosure.
Figure 10B:
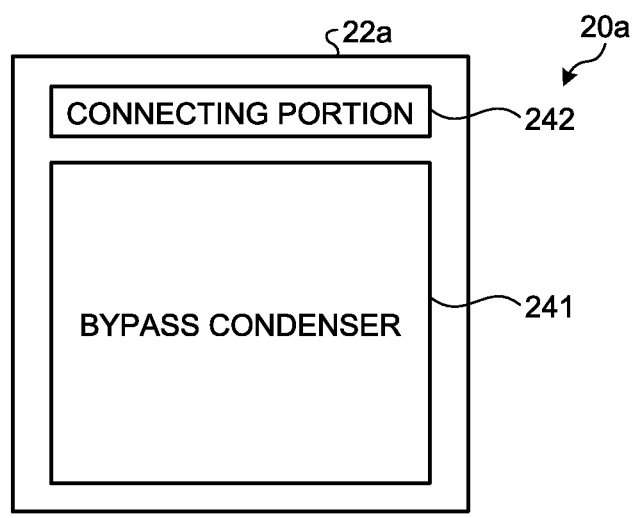
FIG. 10B is a plan view schematically illustrating a second chip forming the imaging element according to the modified example of the first embodiment of the disclosure.
Figure 10C:
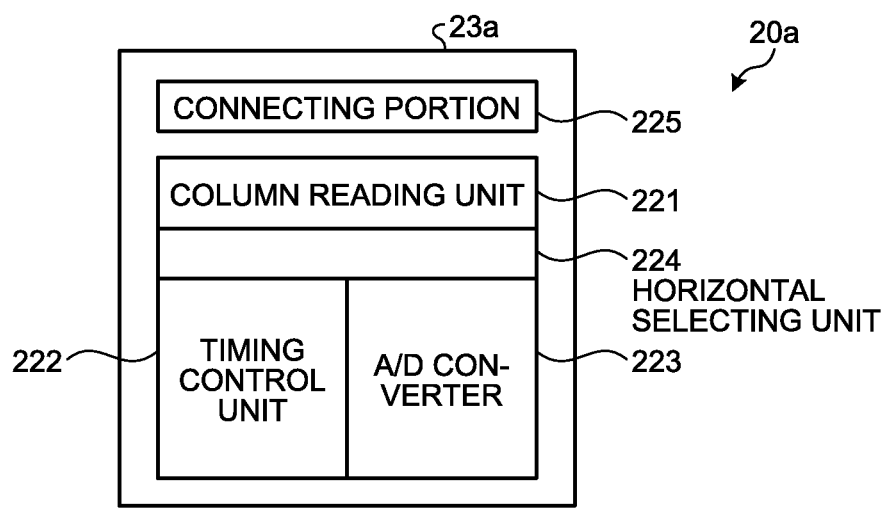
FIG. 10C is a plan view schematically illustrating a third chip forming the imaging element according to the modified example of the first embodiment of the disclosure.
Figure 10D:
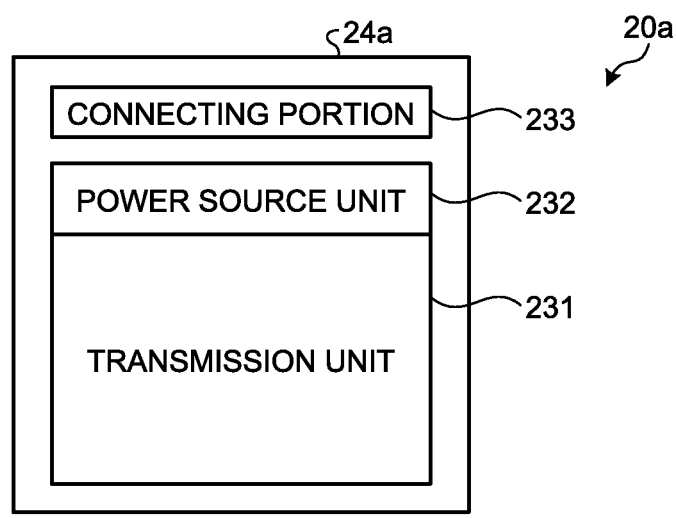
FIG. 10D is a plan view schematically illustrating a fourth chip forming the imaging element according to the modified example of the first embodiment of the disclosure.
Figure 11A:
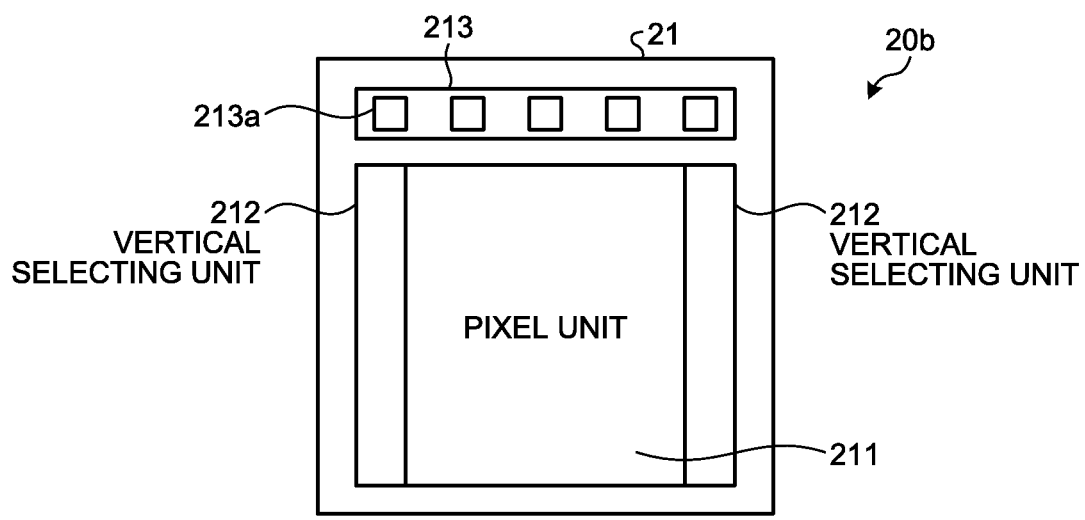
FIG. 11A is a plan view schematically illustrating a first chip forming another imaging element according to the modified example of the first embodiment of the disclosure.
Figure 11B:
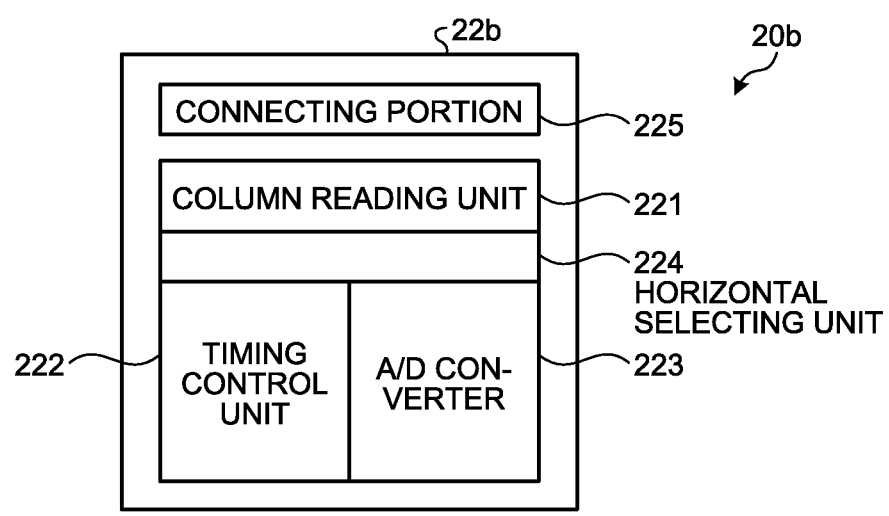
FIG. 11B is a plan view schematically illustrating a second chip forming the other imaging element according to the modified example of the first embodiment of the disclosure.
Figure 11C:
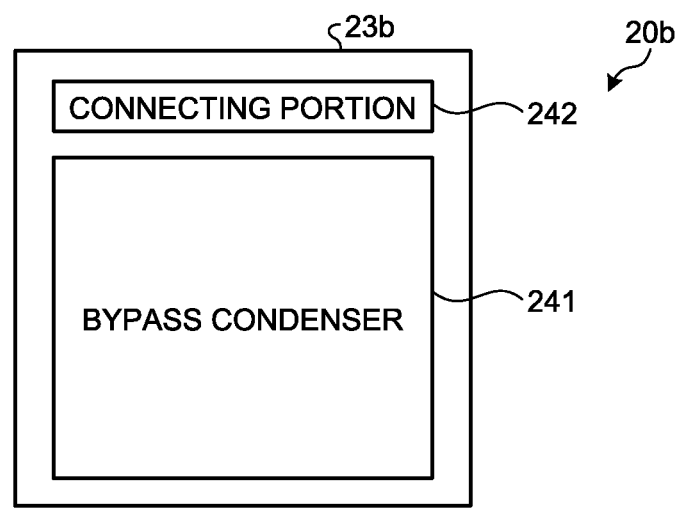
FIG. 11C is a plan view schematically illustrating a third chip forming the other imaging element according to the modified example of the first embodiment of the disclosure.
Figure 11D:
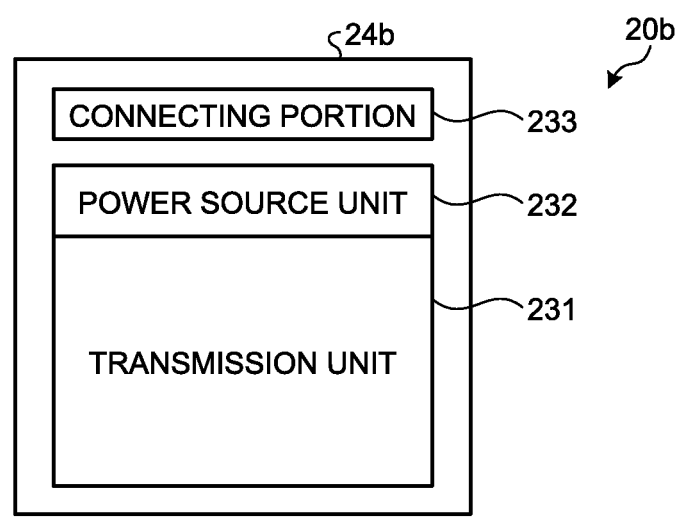
FIG. 11D is a plan view schematically illustrating a fourth chip forming the other imaging element according to the modified example of the first embodiment of the disclosure.

Next, a manufacturing method for the imaging element 20 will be described. FIG. 7 is a flow chart illustrating an outline of the manufacturing method for the imaging element 20. FIG. 8A to FIG. 8N are schematic diagrams illustrating cross sections of the imaging element 20 at the respective manufacturing steps in FIG. 7. Since the imaging element 20 is manufactured by use of a well-known semiconductor manufacturing apparatus, description of the configuration of the semiconductor manufacturing apparatus will hereinafter be omitted.

As illustrated in FIG. 7, firstly, the semiconductor manufacturing apparatus manufactures a CIS wafer, an ADC wafer, an IF wafer, and a capacitative wafer, by forming a semiconductor integrated circuit and a capacitative element on Si wafers by using a known semiconductor integrated circuit process (Step S101). In this case, the semiconductor manufacturing apparatus forms a multi-layered wiring layer, which is formed of: an insulating layer; and an electrically conducting layer, on each wafer. For example, as illustrated in FIG. 8A, the semiconductor manufacturing apparatus forms the first multi-layered wiring layer 25 on the first chip 21.

Subsequently, the semiconductor manufacturing apparatus layers and connects the CIS wafer and ADC wafer together (Step S102). Specifically, as illustrated in FIG. 8B, the semiconductor manufacturing apparatus flattens the first multi-layered wiring layer 25 on the first chip 21 and the second multi-layered wiring layer 26 on the second chip 22, to make heights of the outermost surfaces of the insulating layers substantially the same as heights of the outermost surfaces of the electrically conducting layers respectively, and thereafter sticks together the first multi-layered wiring layer 25 on the first chip 21 and the second multi-layered wiring layer 26 on the second chip 22, with the electrode 31 formed of an electrically conducting layer. Thereby, the insulating layers and the electrically conducting layers are connected collectively (hybrid bonding).

Thereafter, the semiconductor manufacturing apparatus performs thinning of the ADC wafer (Step S103). Specifically, the semiconductor manufacturing apparatus performs, as illustrated in FIG. 8C, from the state in FIG. 8B, thinning of the second chip 22 to about 3 μm to 50 μm. In this case, since the first chip 21 functions as a support wafer, there is no need for a support wafer to be separately used for handling in the thinning of the second chip 22.

Subsequently, the semiconductor manufacturing apparatus layers and connects the ADC wafer and the IF wafer together (Step S104). Specifically, as illustrated in FIG. 8D, the semiconductor manufacturing apparatus layers them together by connecting together the insulating film formed on the thinned surface of the second chip 22 and the insulating film on the third multi-layered wiring layer 27 on the third chip 23.

Thereafter, the semiconductor manufacturing apparatus performs thinning of the IF wafer (Step S105). Specifically, as illustrated in FIG. 8E, the semiconductor manufacturing apparatus performs thinning of the third chip 23.

Subsequently, the semiconductor manufacturing apparatus forms a TSV in each of the ADC wafer and the IF wafer (Step S106). Specifically, as illustrated in FIG. 8F, the semiconductor manufacturing apparatus forms the TSV 32 in each of the second chip 22 and the third chip 23, and connects the second multi-layered wiring layer 26 on the second chip 22 and the third multi-layered wiring layer 27 on the third chip 23 to each other. In this case, for example, by well-known twin contact, shared contact, or the like, the semiconductor manufacturing apparatus connects the second multi-layered wiring layer 26 on the second chip 22 and the third multi-layered wiring layer 27 on the third chip 23 to each other.

Thereafter, the semiconductor manufacturing apparatus layers and connects together the IF wafer and the capacitative wafer (Step S107). Specifically, as illustrated in FIG. 8G, the semiconductor manufacturing apparatus layers and connects them together by connecting the electrode 33, which has been formed on a back surface of the third chip 23 and connects to the TSV 32, and the fourth multi-layered wiring layer 28 on the fourth chip 24, to each other, via hybrid bonding, a bump, or the like.

Subsequently, the semiconductor manufacturing apparatus performs thinning of the capacitative wafer (Step S108). Specifically, as illustrated in FIG. 8H, the semiconductor manufacturing apparatus performs thinning of the fourth chip 24 to about 3 μm to 50 μm.

Thereafter, the semiconductor manufacturing apparatus forms a TSV in the capacitative wafer (Step S109). Specifically, as illustrated in FIG. 8I, the semiconductor manufacturing apparatus forms the TSV 34 that connects to the fourth multi-layered wiring layer 28 on the fourth chip 24.

Subsequently, the semiconductor manufacturing apparatus connects a support wafer to the capacitative wafer (Step S110), and the semiconductor manufacturing apparatus performs thinning of the CIS wafer (Step S111). Specifically, as illustrated in FIG. 8J, after temporarily connecting a support wafer 36 to a back surface of the fourth chip 24, the semiconductor manufacturing apparatus performs thinning of the first chip 21.

Thereafter, the semiconductor manufacturing apparatus opens a probing pad in the CIS wafer (Step S112). Specifically, as illustrated in FIG. 8K, by performing etching processing on the Si substrate and insulating layer at the connecting portion 213 (a connected area) of the first chip 21 so as to expose, as a pad, a part of the first multi-layered wiring layer 25 on the first chip 21, the semiconductor manufacturing apparatus forms the probing pad 213a.

Subsequently, the semiconductor manufacturing apparatus forms an on-chip filter (OCF), such as a color filter or a micro-lens, on the CIS wafer (Step S113).

Thereafter, an inspection apparatus, which is not illustrated in the drawings, inspects the layered wafers (Step S114). Specifically, the inspection apparatus performs image inspection on the imaging element 20 (the layered wafers) by probing the probing pad 213a with an inspection probe.

Subsequently, the semiconductor manufacturing apparatus bonds a cover glass to the CIS wafer (Step S115). Specifically, as illustrated in FIG. 8L, the semiconductor manufacturing apparatus bonds the cover glass 30 (the cover glass wafer) onto the OCF on the first chip 21.

Thereafter, the semiconductor manufacturing apparatus performs peeling of the support wafer (Step S116). Specifically, as illustrated in FIG. 8M, the semiconductor manufacturing apparatus peels off the support wafer 36 from the back surface of the fourth chip 24.

Subsequently, the semiconductor manufacturing apparatus forms an electrode on the back surface of the IF wafer (Step S117). Specifically, as illustrated in FIG. 8N, the semiconductor manufacturing apparatus forms the electrode 35 for external connection, on the back surface of the fourth chip 24. The semiconductor manufacturing apparatus thus manufactures the imaging element 20 to be used in this first embodiment, and ends this processing.

Herein, as an example, the method where the thinning of the capacitative wafer (Step S108) and the TSV formation in the capacitative wafer (Step S109) are performed before the thinning of the CIS wafer (Step S111) has been described, but the thinning of the CIS wafer (Step S111), the opening of the probing pad in the CIS wafer (Step S112), the formation of the on-chip filter (OCF) on the CIS wafer (Step S113), the inspection of the layered wafers (Step S114), and the bonding of the cover glass to the CIS wafer (Step S115) may be performed before the thinning of the capacitative wafer (Step S108) and the TSV formation in the capacitative wafer (Step S109). In this case, since the capacitative wafer before the thinning processing functions as a support wafer in the thinning of the CIS wafer, steps for temporary connection and peeling of a support wafer are not separately needed, and the process is thus able to be simplified.

Operation of Imaging Element

Next, operation of the imaging element 20 will be described. FIG. 9 is a timing chart illustrating the operation of the imaging element 20. In FIG. 9, the horizontal axis represents time. Further, (a) in FIG. 9 indicates timing for horizontal line reading in the pixel unit 211, (b) in FIG. 9 indicates AD conversion timing of the second chip 22, and (c) in FIG. 9 indicates transmission timing by the transmission unit 231 of the third chip 23. A line N and a line N+1 in the pixel unit 211 in FIG. 9 will be described as an example.

As illustrated in FIG. 9, the timing control unit 222 starts reading of the line N in the pixel unit 211 (time t1), A/D converts an analog imaging signal read out from an odd column into a digital imaging signal, and causes this digital imaging signal to be transmitted by the transmission unit 231 to the transmission cable 3 (time t2 to time t3).

Thereafter, after a horizontal blanking period (time t4), the timing control unit 222 A/D converts an analog imaging signal read out from an even column into a digital imaging signal, and causes this digital imaging signal to be transmitted by the transmission unit 231 to the transmission cable 3 (time t4 to time t5).

Subsequently, the timing control unit 222 starts reading of the line N+1 in the pixel unit 211 (time t5).

Thereafter, after a horizontal blanking period (time t6), the timing control unit 222 A/D converts an analog imaging signal read out from the odd column into a digital imaging signal, and causes this digital imaging signal to be transmitted by the transmission unit 231 to the transmission cable 3 (time t6 to time t7).

Subsequently, after a horizontal blanking period (time t8), the timing control unit 222 A/D converts an analog imaging signal read out from the even column into a digital imaging signal, and causes this digital imaging signal to be transmitted by the transmission unit 231 to the transmission cable 3 (time t8 to time t9).

As described above, per horizontal line in the pixel unit 211, the timing control unit 222 directly transmits the digital imaging signals to the transmission cable 3 in the order from the odd column to the even column.

According to the above described first embodiment of the disclosure, since the connecting portion 213, the connecting portion 225, and the connecting portion 242 that the first chip 21, the second chip 22, and the fourth chip 24 (the capacitative chip) have are arranged to overlap one another as viewed in the direction orthogonal to the light receiving surface of the pixel unit 211, further downsizing is able to be realized.

Further, according to the first embodiment of the disclosure, since a timing adjusting circuit for adjustment of variation among the chips is able to be omitted by the arrangement of the column reading unit 221, the timing control unit 222, the A/D converter 223, and the horizontal selecting unit 224 on the same second chip 22, the imaging element 20 is able to be downsized even more.

Further, according to the first embodiment of the disclosure, since the pixel unit 211 is arranged on the first chip 21, the A/D converter 223 is arranged on the second chip 22, and the transmission unit 231 is arranged on the third chip 23, noise is able to be prevented from reaching the pixel unit 211 from the digital circuits.

Further, according to the first embodiment of the disclosure, since the probing pad 213a is formed in the first chip 21 such that the probing pad 213a overlaps the connecting portion 213 as viewed from the light receiving surface side of the pixel unit 211, the imaging element 20 is able to be manufactured while image inspection is being performed before packaging (before cutting from the wafers or before incorporation in the endoscope 2) without increase in the chip size of the imaging element 20.

Although there is only one fourth chip 24 serving as the capacitative chip in the first embodiment of the disclosure, plural capacitative chips may be layered and connected.

Modified Example of First Embodiment

Next, a modified example of the first embodiment of the disclosure will be described. According to the above described first embodiment, the bypass condenser 241 is formed on the fourth chip 24, but a layer to be formed with a bypass condenser may be changed as appropriate. FIG. 10A to FIG. 10D are plan views schematically illustrating chips forming an imaging element according to the modified example of the first embodiment. FIG. 11A to FIG. 11D are plan views schematically illustrating chips forming another imaging element according to the modified example of the first embodiment. The same reference signs will be assigned to configurations that are the same as those of the above described endoscope system 1 according to the first embodiment, and description thereof will be omitted.

As illustrated in FIG. 10A to FIG. 10D, an imaging element 20a includes the first chip 21, a second chip 22a, a third chip 23a, and a fourth chip 24a, and these chips are layered over one another. Further, the imaging element 20a includes: the bypass condenser 241 formed on the second chip 22a; the column reading unit 221, the timing control unit 222, the A/D converter 223, and the horizontal selecting unit 224 that are formed on the third chip 23a; and the transmission unit 231 and the power source unit 232 that are formed on the fourth chip 24a.

Further, as illustrated in FIG. 11A to FIG. 11D, an imaging element 20b includes the first chip 21, a second chip 22b, a third chip 23b, and a fourth chip 24b, and these chips are layered over one another. Furthermore, the imaging element 20b includes the bypass condenser 241 formed on the third chip 23b, and the transmission unit 231 and the power source unit 232 that are formed on the fourth chip 24b.

According to the above described modified example of the first embodiment of the disclosure, by the bypass condenser 241 being layered near the first chip 21 having the pixel unit 211 formed thereon, reach of power source noise to the pixel unit 211 is able to be reduced even more.

Further, according to the modified example of the first embodiment of the disclosure, distances between: the first chip 21 (the CIS chip); and the third chip 23a and the second chip 22b (the ADC chips) that are heat sources, or the fourth chip 24a and the fourth chip 24b (the IF chips) that are heat sources are able to be increased, and thus unevenness of images due to non-uniformity of temperature of the respective pixels 211a is able to be prevented.

According to the modified example of the first embodiment of the disclosure, the capacitative chip having the bypass condenser 241 arranged thereon is layered and connected between the CIS chip and the ADC chip or between the ADC chip and the IF chip, but for example, capacitative chips may be layered and connected between the respective chips. Specifically, a capacitative chip may each be provided between the CIS chip and the ADC chip, and between the ADC chip and the IF chip. Of course, one or plural capacitative chips may be layered and connected onto the back surface of the IF chip.

Second Embodiment

Next, a second embodiment of the disclosure will be described. A configuration of an imaging element according to this second embodiment is different from the above described configuration of the imaging element 20 according to the first embodiment. Specifically, in the above described imaging element 20 according to the first embodiment, imaging signals are directly read out respectively from an odd column and an even column and transmitted to the transmission cable 3, but according to this second embodiment, imaging signals respectively read out from an odd column and an even column are temporarily recorded and transmitted to the transmission cable 3. Hereinafter, after the configuration of the imaging element according to the second embodiment is described, drive timing for the imaging element will be described. The same reference signs will be assigned to configurations that are the same as those of the above described endoscope system 1 according to the first embodiment, and description thereof will be omitted.

Figure 12:
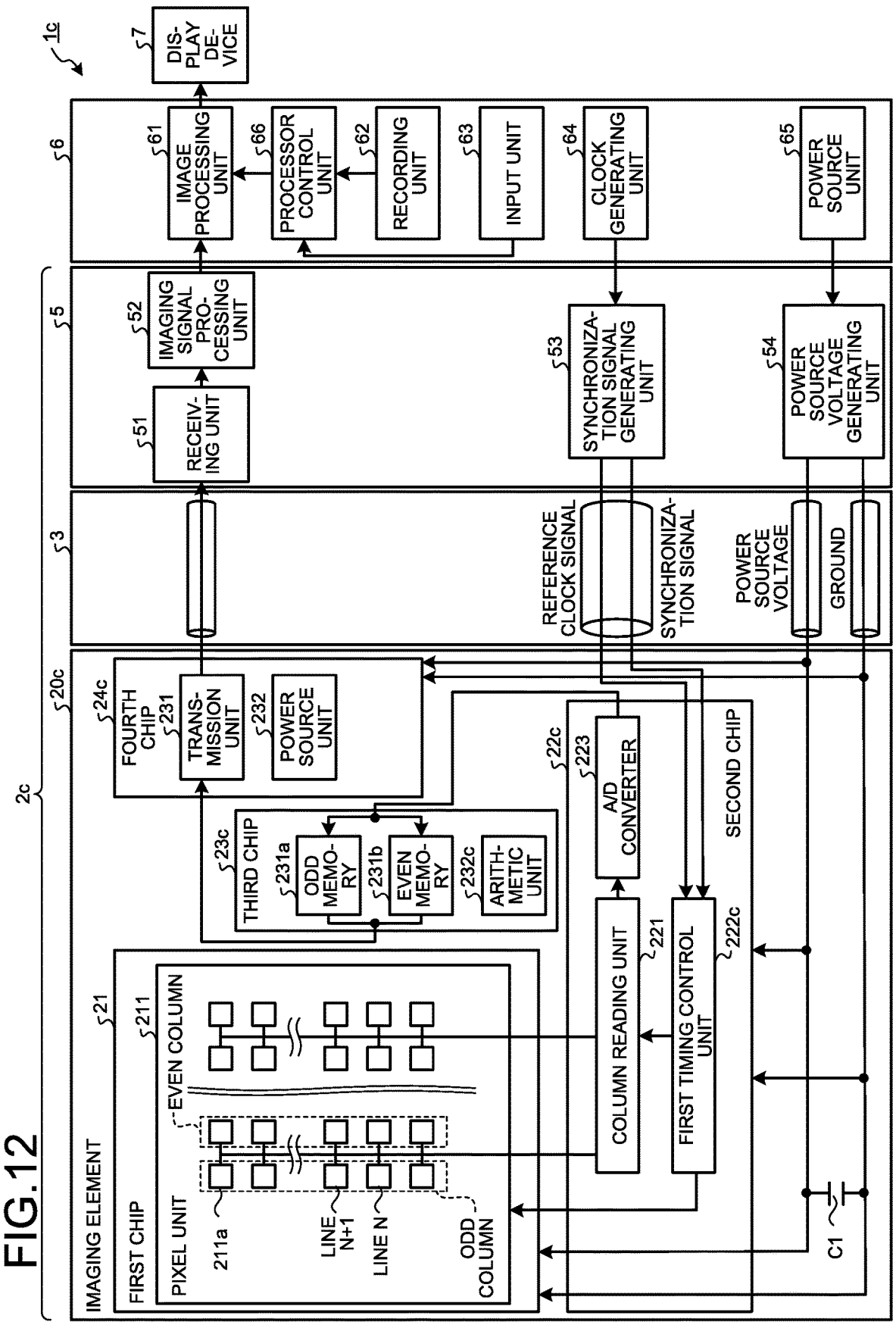
FIG. 12 is a block diagram illustrating functions of main parts of an endoscope system according to a second embodiment of the disclosure.

FIG. 12 is a block diagram illustrating functions of main parts of an endoscope system according to the second embodiment of the disclosure. An endoscope system 1c illustrated in FIG. 12 includes an endoscope 2c, instead of the above described endoscope 2 of the endoscope system 1 according to the first embodiment.

Instead of the above described imaging element 20 of the endoscope 2 according to the first embodiment, the endoscope 2c includes an imaging element 20c. The imaging element 20c includes the first chip 21, a second chip 22c, a third chip 23c, and a fourth chip 24c.

The second chip 22c includes: the column reading unit 221; a first timing control unit 222c (a first timing circuit) that generates a drive signal for control of driving of each part forming the imaging element 20c; and the A/D converter 223.

The third chip 23c includes: an odd memory 231a that temporarily records therein an imaging signal read out from an odd column; an even memory 231b that temporarily records therein an imaging signal read out from an even column; and an arithmetic unit 232c (an arithmetic circuit) that executes various arithmetic operations.

The fourth chip 24c includes the transmission unit 231 and the power source unit 232.

Structure of Imaging Element

Figure 13A:
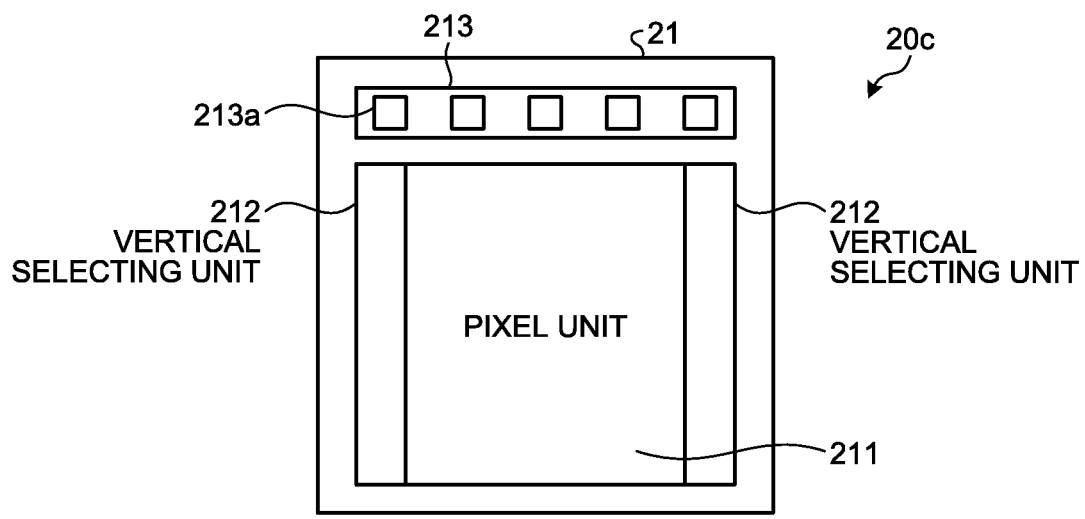
FIG. 13A is a plan view schematically illustrating a first chip forming an imaging element according to the second embodiment of the disclosure.
Figure 13B:
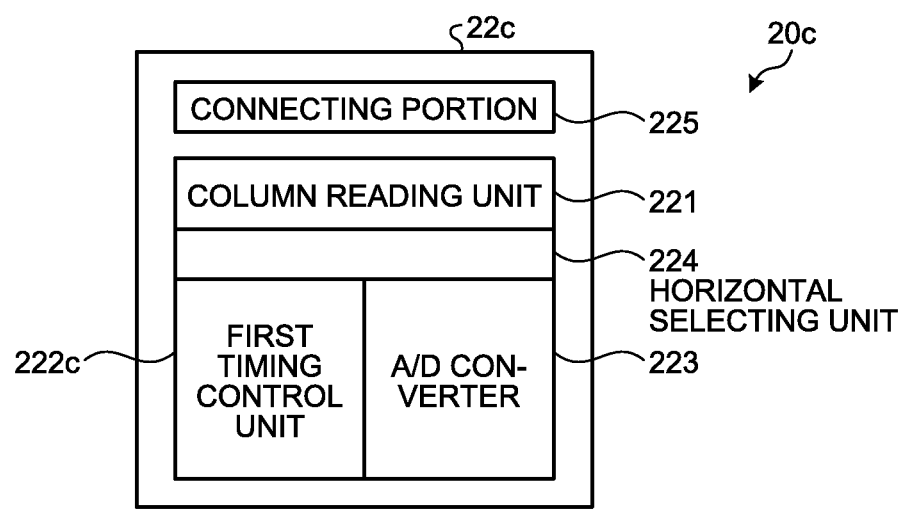
FIG. 13B is a plan view schematically illustrating a second chip forming the imaging element according to the second embodiment of the disclosure.
Figure 13C:
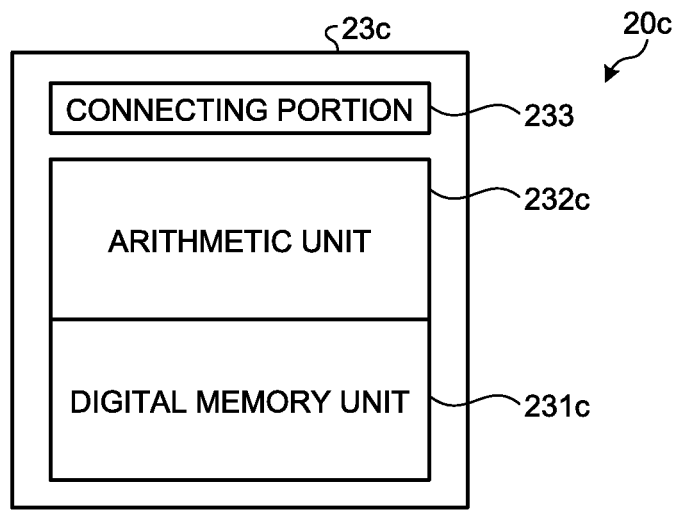
FIG. 13C is a plan view schematically illustrating a third chip forming the imaging element according to the second embodiment of the disclosure.
Figure 13D:
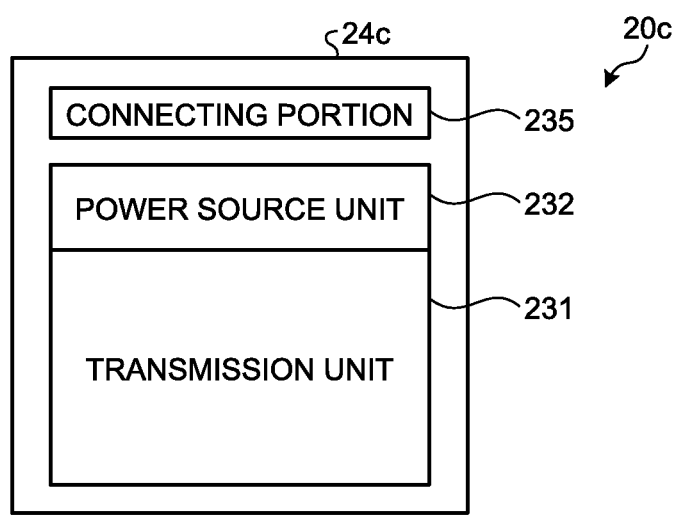
FIG. 13D is a plan view schematically illustrating a fourth chip forming the imaging element according to the second embodiment of the disclosure.

Next, a detailed structure of the above described imaging element 20c will be described. FIG. 13A is a plan view schematically illustrating the first chip 21 forming the imaging element 20c. FIG. 13B is a plan view schematically illustrating the second chip 22c forming the imaging element 20c. FIG. 13C is a plan view schematically illustrating the third chip 23c forming the imaging element 20c. FIG. 13D is a plan view schematically illustrating the fourth chip 24c forming the imaging element 20c.

The second chip 22c includes, as illustrated in FIG. 13B, the column reading unit 221, the first timing control unit 222c, the A/D converter 223, the horizontal selecting unit 224, and the connecting portion 225.

The third chip 23c includes, as illustrated in FIG. 13C: the arithmetic unit 232c (the arithmetic circuit); a digital memory unit 231c (a digital memory circuit) that temporarily records therein an imaging signal read out by the column reading unit 221; and the connecting portion 233. The digital memory unit 231c is formed of the above described odd memory 231a and even memory 231b.

The fourth chip 24c includes the transmission unit 231, the power source unit 232, and a connecting portion 235.

Operation of Imaging Element

Next, operation of the imaging element 20c will be described. FIG. 14 is a timing chart illustrating the operation of the imaging element 20c. In FIG. 14, the horizontal axis represents time. Further, (a) in FIG. 14 indicates timing for horizontal line reading in the pixel unit 211, (b) in FIG. 14 indicates AD conversion timing of the second chip 22c, (c) in FIG. 14 indicates write and read timing for an imaging signal, which has been read out from an odd column, into and from the digital memory unit 231c, (d) in FIG. 14 indicates write and read timing of an imaging signal, which has been read out from an even column, into and from the digital memory unit 231c, and (e) in FIG. 14 indicates transmission timing by the transmission unit 231. The line N and the line N+1 in the pixel unit 211 in FIG. 14 will be described as an example.

As illustrated in FIG. 14, the first timing control unit 222c starts reading the line N in the pixel unit 211 (time t11), A/D converts an analog imaging signal read out from an odd column into a digital imaging signal, and writes this digital imaging signal into the digital memory unit 231c (the odd memory 231a) (time t12 to time t13).

Subsequently, the first timing control unit 222c reads out the odd column's imaging signal that has been written into the digital memory unit 231c (the odd memory 231a) according to timing of a horizontal blanking period (time t13), and starts line N's odd column transmission for transmission of the imaging signal of the odd column of the line N by the transmission unit 231 to the transmission cable 3 (time t13).

Thereafter, after a horizontal blanking period (time t14), the first timing control unit 222c A/D converts an analog imaging signal read out from an even column, into a digital imaging signal, and writes this digital imaging signal into the digital memory unit 231c (the even memory 231b) (time t14 to time t15).

Subsequently, after the transmission of the imaging signal of the odd column of the line N (time t15), the first timing control unit 222c starts reading the line N+1 in the pixel unit 211 (time t15).

Thereafter, the first timing control unit 222c reads the even column's imaging signal that has been written into the digital memory unit 231c (the even memory 231b) according to timing of a horizontal blanking period (time t15), and starts line N's even column transmission for transmission of the imaging signal of the even column of the line N by the transmission unit 231 to the transmission cable 3 (time t15).

Subsequently, after a horizontal blanking period (time t16), the first timing control unit 222c A/D converts an analog imaging signal read out from the odd column into a digital imaging signal, and writes this digital imaging signal into the digital memory unit 231c (the odd memory 231a) (time t16 to time t17).

Thereafter, after the transmission of the imaging signal of the even column of the line N (time t17); according to timing of a horizontal blanking period (time t17), reading of the odd column's imaging signal that has been written into the digital memory unit 231c (the odd memory 231a) is performed, and line N+1's odd column transmission for transmission of the imaging signal of the odd column of the line N+1 by the transmission unit 231 to the transmission cable 3 is started (time t17).

Subsequently, after a horizontal blanking period (time t18), the first timing control unit 222c A/D converts an analog imaging signal read out from the even column into a digital imaging signal, and writes this digital imaging signal into the digital memory unit 231c (the even memory 231b) (time t18 to time t19).

Thereafter, according to timing of a horizontal blanking period (time t19), reading of the even column's imaging signal that has been written into the digital memory unit 231c is performed, and line N+1's even column transmission for transmission of the imaging signal of the even column of the line N+1 by the transmission unit 231 to the transmission cable 3 is started (time t19).

According to the above described second embodiment of the disclosure, downsizing is able to be realized, similarly to the first embodiment.

Further, according to the second embodiment of the disclosure, by the A/D converted imaging signals being held through the provision of the odd memory 231a and even memory 231b on the third chip 23c, the transmission rate is able to be reduced, and variation in the column circuit forming the column reading unit 221 is able to be corrected.

In this second embodiment of the disclosure, the capacitative chip having the bypass condenser 241 formed thereon may be layered and connected between any of: the first chip 21 and the second chip 22c; between the second chip 22c and the third chip 23c; and between the third chip 23c and the fourth chip 24c. Of course, one or plural capacitative chips may be layered and connected onto a back surface of the fourth chip 24c.

Third Embodiment

Next, a third embodiment of the disclosure will be described. A configuration of an endoscope according to the third embodiment is different from the above described configuration of the endoscope 2 according to the first embodiment. Specifically, in the above described endoscope 2 according to the first embodiment, a parallel signal is transmitted to the transmission unit 231 from the A/D converter 223, but in this third embodiment, a parallel signal is converted to a serial signal and the serial signal is transmitted to a transmission unit. Hereinafter, the configuration of the endoscope according to the third embodiment will be described. The same reference signs will be assigned to configurations that are the same as those of the above described endoscope system 1 according to the first embodiment, and description thereof will be omitted.

Figure 15:
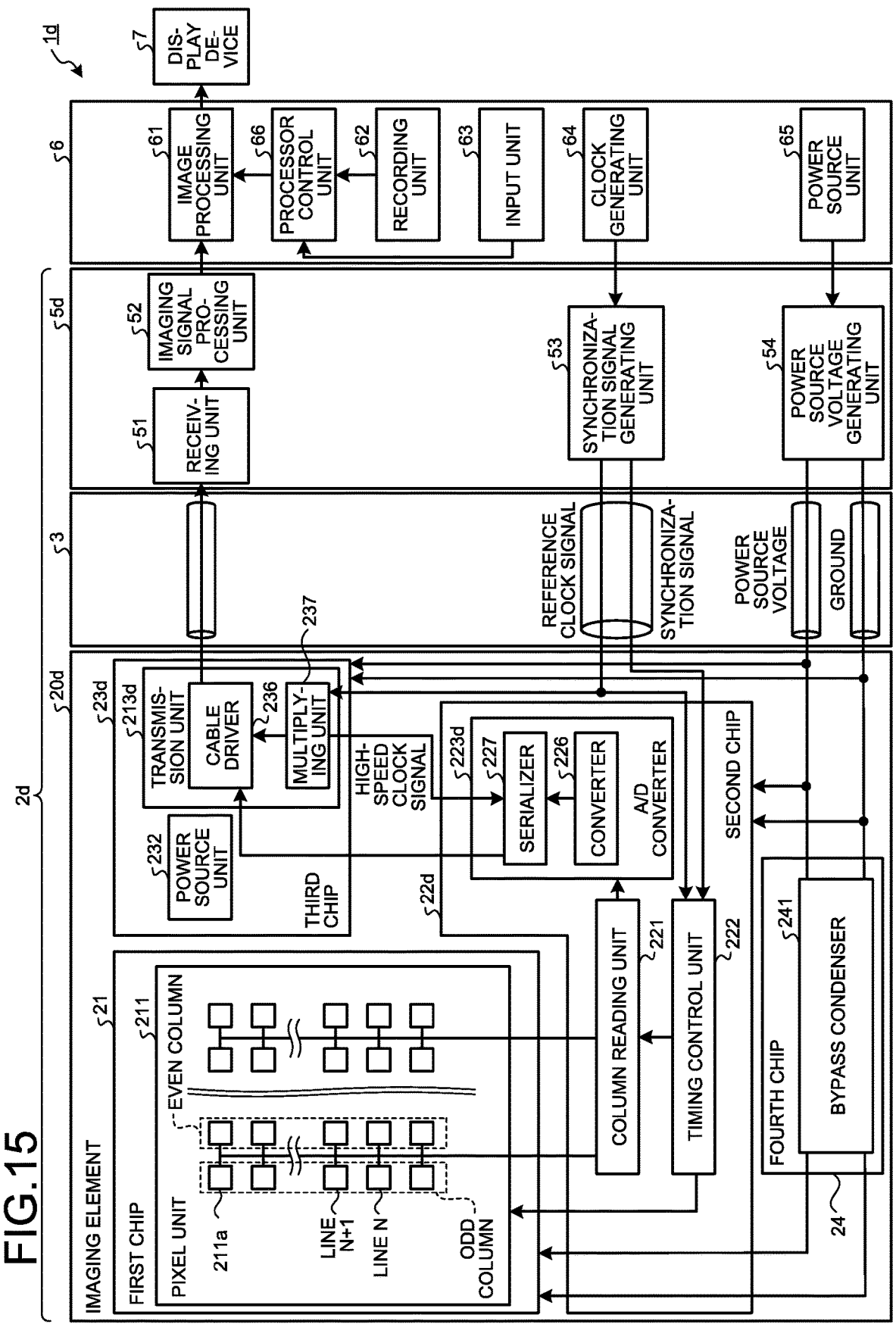
FIG. 15 is a block diagram illustrating functions of main parts of an endoscope system according to a third embodiment of the disclosure.

FIG. 15 is a block diagram illustrating functions of main parts of an endoscope system according to the third embodiment. An endoscope system 1d illustrated in FIG. 15 includes an endoscope 2d, instead of the above described endoscope 2 of the endoscope system 1 according to the first embodiment.

The endoscope 2d includes, instead of the above described imaging element 20 and connector unit 5 according to the first embodiment, an imaging element 20d and a connector unit 5d.

The imaging element 20d includes, instead of the above described second chip 22 and third chip 23 according to the first embodiment, a second chip 22d and a third chip 23d.

The second chip 22d includes the column reading unit 221, the timing control unit 222, and an A/D converter 223d.

The A/D converter 223d includes: a converter 226 that A/D converts an analog imaging signal into a digital imaging signal; and a serializer 227 that converts the parallel imaging signal that has been converted by the converter 226, into a serial imaging signal, and that transmits the serial imaging signal to the third chip 23d. Based on a high-speed clock signal input from a multiplying unit 237 of the third chip 23d described later, the serializer 227 converts the parallel imaging signal into the serial imaging signal, and transmits the serial imaging signal to the third chip 23d.

The third chip 23d includes the power source unit 232 and a transmission unit 213d. The transmission unit 213d includes a cable driver 236 and the multiplying unit 237 (a multiplying circuit).

Based on a high-speed clock signal input from the multiplying unit 237, the cable driver 236 transmits the serial imaging signal input from the serializer 227, to the transmission cable 3, by a differential method (for example, LVDS).

The multiplying unit 237 is configured by use of a phase locked loop (PLL). The multiplying unit 237 converts a frequency of a reference clock signal input from the connector unit 5d, to a frequency that is n times (for example, twice or thrice) that frequency, and outputs the converted reference clock signal to the cable driver 236 and the serializer 227. Specifically, based on the number of bits (for example, eight bits) of the A/D converter 223d, the multiplying unit 237 outputs a high-speed clock signal resulting from multiplication of a clock signal.

According to the above described third embodiment of the disclosure, since wiring connecting together the second chip 22d and the third chip 23d, for example, the number of connections for the TSV 32, is able to be reduced, the area of the connecting portions in the imaging element 20d is able to be reduced.

Fourth Embodiment

Next, a fourth embodiment of the disclosure will be described. A configuration of an imaging element according to this fourth embodiment is different from the above described configuration of the imaging element 20 according to the first embodiment. Specifically, in the above described imaging element 20 according to the first embodiment, a digital imaging signal is transmitted to the transmission cable 3, but in this fourth embodiment, an analog imaging signal is transmitted to the transmission cable 3. The transmitted analog imaging signal is converted into a digital signal by an analog front-end unit additionally included in the receiving unit 51, and the digital signal is output to the processor 6 via the imaging signal processing unit 52. Hereinafter, the configuration of the imaging element according to the fourth embodiment will be described. The same reference signs will be assigned to configurations that are the same as those of the above described endoscope system 1 according to first embodiment, and description thereof will be omitted.

Structure of Imaging Device

Figure 16A:
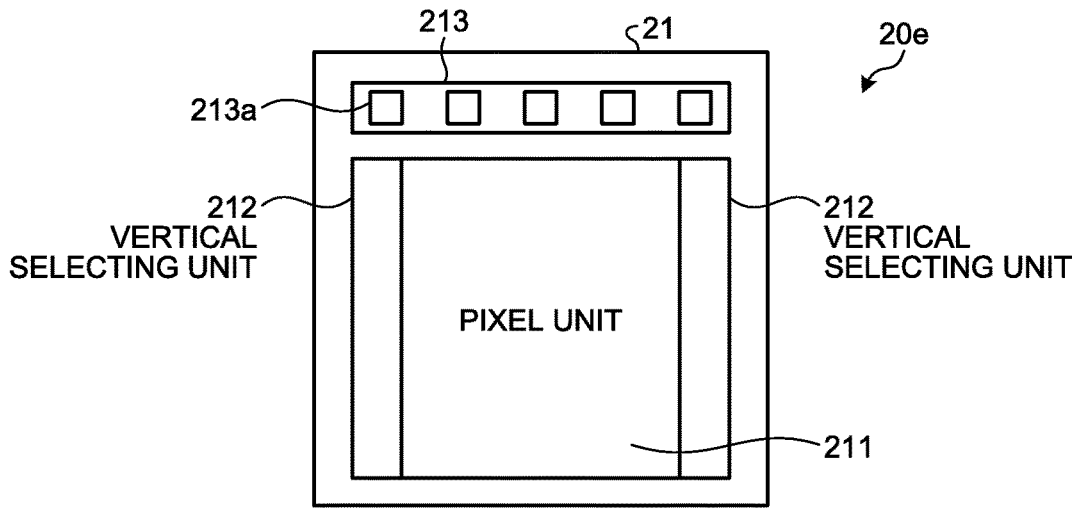
FIG. 16A is a plan view of a first chip of an imaging element according to a fourth embodiment of the disclosure.
Figure 16B:
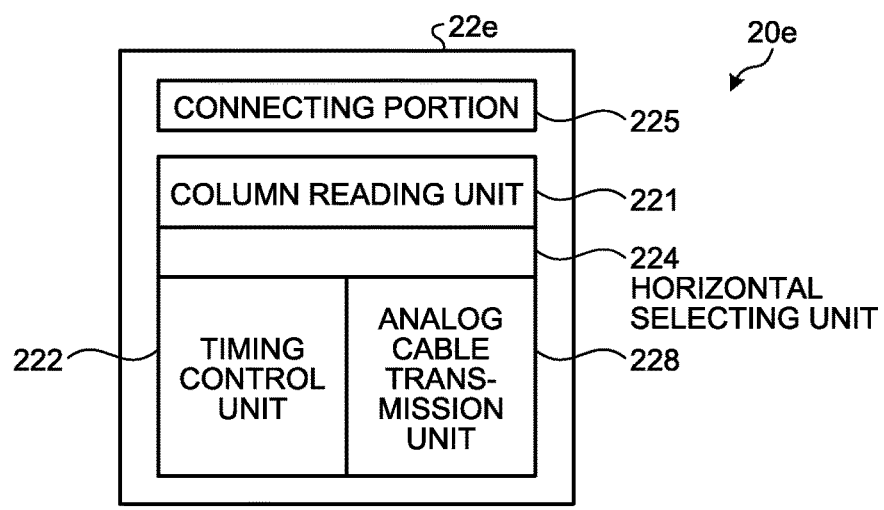
FIG. 16B is a plan view of a second chip of the imaging element according to the fourth embodiment of the disclosure.
Figure 16C:
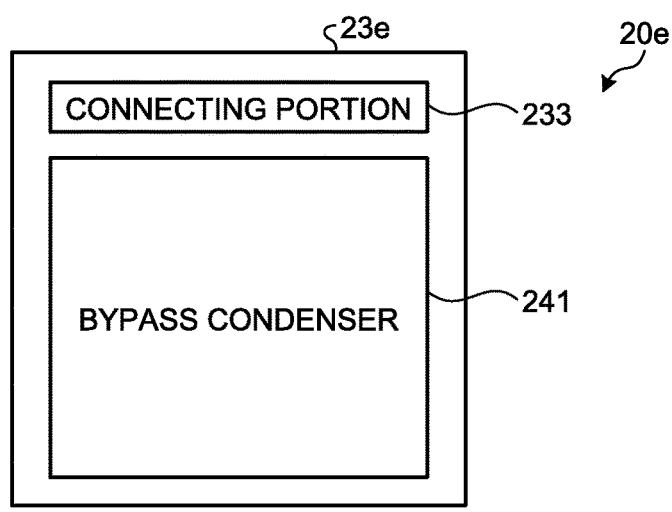
FIG. 16C is a plan view of a third chip of the imaging element according to the fourth embodiment of the disclosure.

FIG. 16A is a plan view of a first chip of the imaging element according to the fourth embodiment. FIG. 16B is a plan view of a second chip of the imaging element according to the fourth embodiment. FIG. 16C is a plan view of a third chip of the imaging element according to the fourth embodiment.

As illustrated in FIG. 16A to FIG. 16C, an imaging element 20e includes the first chip 21, a second chip 22e, and a third chip 23e. The imaging element 20e is formed of the third chip 23e, the second chip 22e, the first chip 21, and the cover glass 30 (not illustrated in the drawings), which are layered over one another in this order along the direction orthogonal to the plane of the pixel unit 211 on the first chip 21.

The second chip 22e includes the column reading unit 221, the horizontal selecting unit 224, the timing control unit 222, and an analog cable transmission unit 228 (an analog cable transmission circuit) that transmits an analog imaging signal read out by the column reading unit 221, to the transmission cable 3. Further, the second chip 22e includes the connecting portion 225 that electrically connects the respective layers.

The third chip 23e includes the bypass condenser 241 and the connecting portion 233.

According to the above described fourth embodiment of the disclosure, similarly to the above described first embodiment, downsizing of the imaging element 20e is able to be realized.

Fifth Embodiment

Next, a fifth embodiment of the disclosure will be described. A configuration of an imaging element according to this fifth embodiment is different from the above described configuration of the imaging element 20 according to the first embodiment. Hereinafter, the configuration of the imaging element according to the fifth embodiment will be described. The same reference signs will be assigned to configurations that are the same as those of the above described endoscope system 1 according to the first embodiment.

Configuration of Imaging Element

Figure 17:
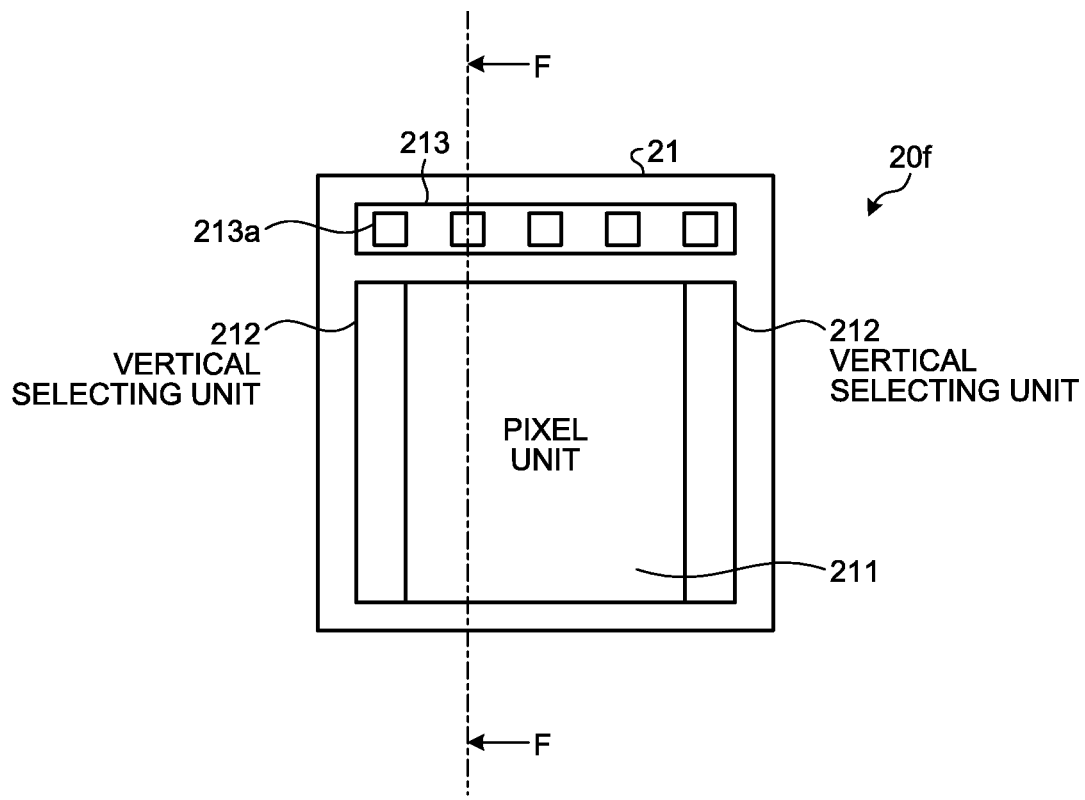
FIG. 17 is a top view of an imaging element according to a fifth embodiment of the disclosure.
Figure 18:
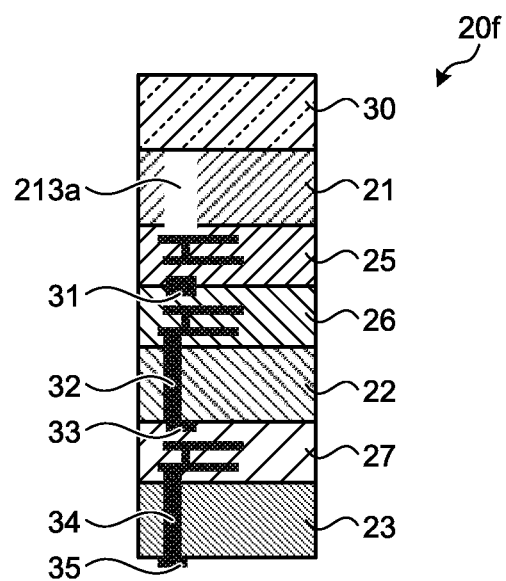
FIG. 18 is a sectional view along a line F-F in FIG. 17.
Figure 19A:
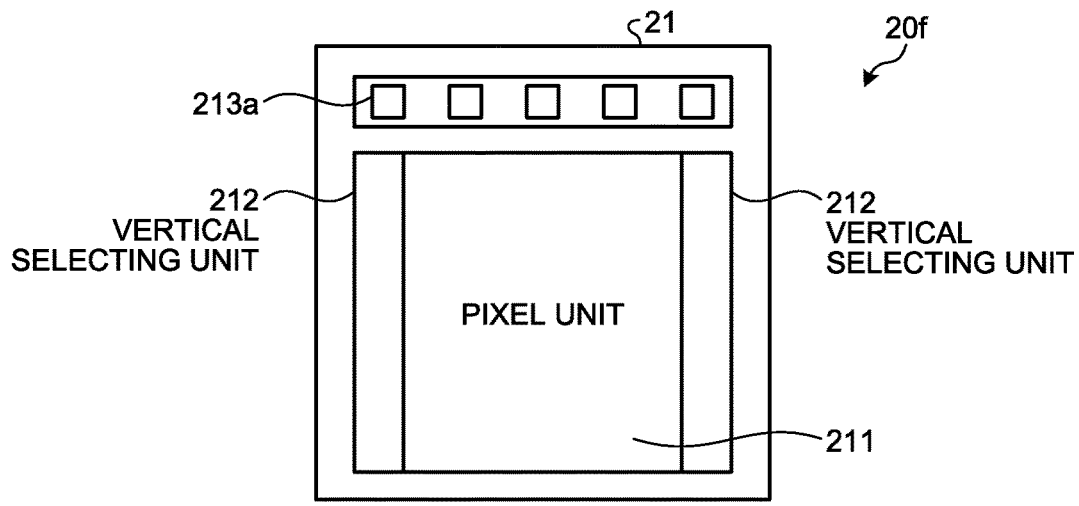
FIG. 19A is a plan view of a first chip of the imaging element according to the fifth embodiment of the disclosure.
Figure 19B:
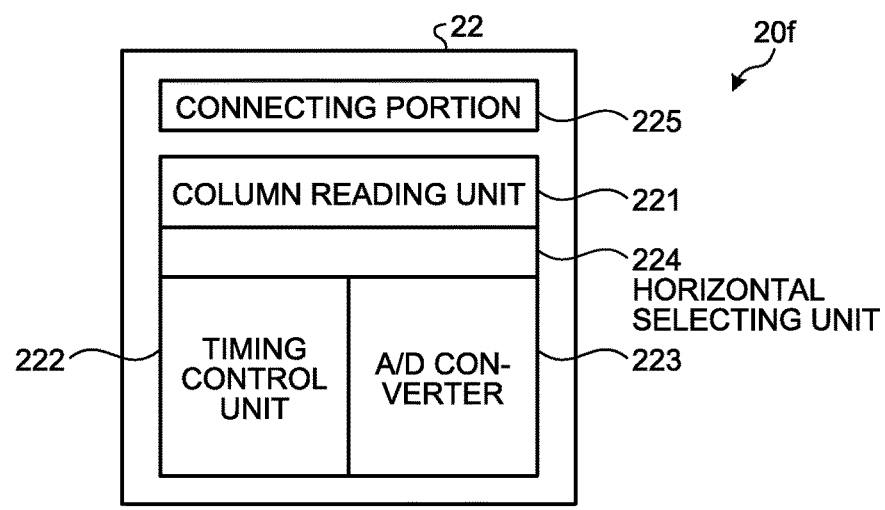
FIG. 19B is a plan view of a second chip of the imaging element according to the fifth embodiment of the disclosure.
Figure 19C:
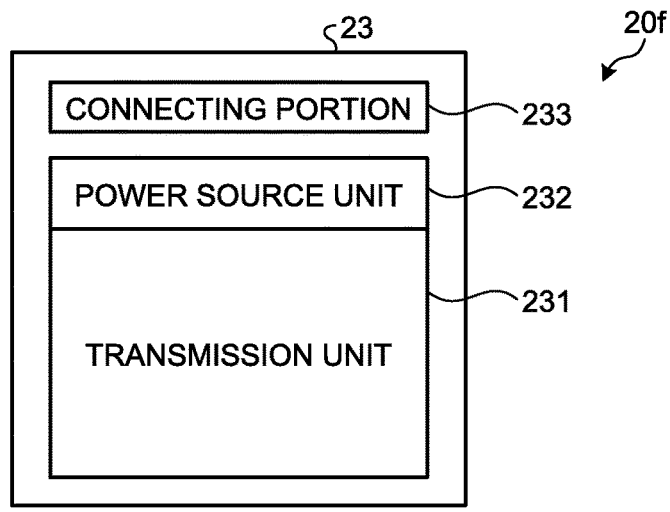
FIG. 19C is a plan view of a third chip of the imaging element according to the fifth embodiment of the disclosure.

FIG. 17 is a top view of the imaging element according to the fifth embodiment. FIG. 18 is a sectional view along a line F-F in FIG. 17. FIG. 19A is a plan view of a first chip of the imaging element according to the fifth embodiment. FIG. 19B is a plan view of a second chip of the imaging element according to the fifth embodiment. FIG. 19C is a plan view of a third chip of the imaging element according to the fifth embodiment.

As illustrated in FIG. 17, FIG. 18, and FIG. 19A to FIG. 19C, an imaging element 20f includes the first chip 21, the second chip 22, and the third chip 23. The imaging element 20f includes the third chip 23, the third multi-layered wiring layer 27, the second chip 22, the second multi-layered wiring layer 26, the first multi-layered wiring layer 25, the first chip 21, and the cover glass 30, which are layered over one another in this order along the direction orthogonal to the plane of the pixel unit 211 on the first chip 21.

Manufacturing Method for Imaging Element

Next, a manufacturing method for the imaging element 20f will be described. FIG. 20 is a flow chart illustrating an outline of the manufacturing method for the imaging element 20f. FIG. 21A to FIG. 21J are schematic diagrams illustrating cross sections of the imaging element 20f at the respective manufacturing steps in FIG. 20. Hereinafter, since the imaging element 20f is manufactured by use of a well-known semiconductor manufacturing apparatus, description of the configuration of the semiconductor manufacturing apparatus will be omitted.

Figure 21A:
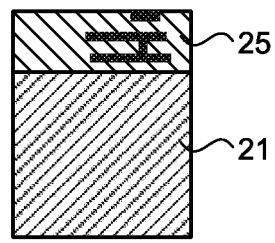
FIG. 21A is a schematic diagram illustrating a cross section of the imaging element at a manufacturing step in FIG. 20.

As illustrated in FIG. 20, firstly, the semiconductor manufacturing apparatus manufactures each of the CIS wafer (the first chip 21), the ADC wafer (the second chip 22), and the IF wafer (the third chip 23), by forming a semiconductor integrated circuit on a Si wafer by using a known semiconductor manufacturing process (Step S201). In this case, the semiconductor manufacturing apparatus forms a multi-layered wiring layer, which is formed of an insulating layer and an electrically conducting layer, on each wafer. For example, as illustrated in FIG. 21A, the semiconductor manufacturing apparatus forms the first multi-layered wiring layer 25 on the first chip 21.

Figure 21B:
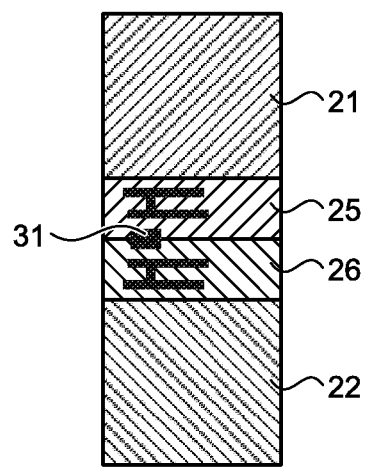
FIG. 21B is a schematic diagram illustrating a cross section of the imaging element at a manufacturing step in FIG. 20.

Subsequently, the semiconductor manufacturing apparatus layers and connects together the CIS wafer and ADC wafer (Step S202). Specifically, as illustrated in FIG. 21B, the semiconductor manufacturing apparatus flattens the first multi-layered wiring layer 25 on the first chip 21 and the second multi-layered wiring layer 26 on the second chip 22, to make heights of the outermost surfaces of the insulating layers substantially the same as the outermost surfaces of the electrically conducting layers respectively, and thereafter sticks together the first multi-layered wiring layer 25 on the first chip 21 and the second multi-layered wiring layer 26 on the second chip 22, with the electrode 31 formed of an electrically conducting layer. Thereby, the insulating layers and the electrically conducting layers are connected collectively (hybrid bonding).

Figure 21C:
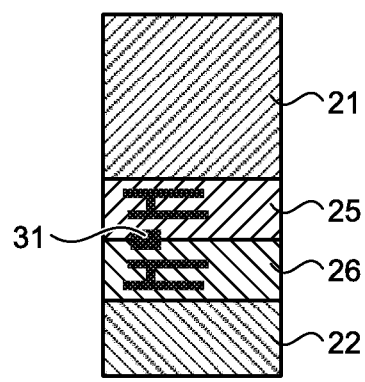
FIG. 21C is a schematic diagram illustrating a cross section of the imaging element at a manufacturing step in FIG. 20.

Thereafter, the semiconductor manufacturing apparatus performs thinning of the ADC wafer (Step S203). Specifically, the semiconductor manufacturing apparatus performs, as illustrated in FIG. 21C, from the state in FIG. 21B, thinning of the second chip 22 to about 3 μm to 50 μm. In this case, since the first chip 21 functions as a support wafer, there is no need for a support wafer to be separately used for handling in the thinning of the second chip 22.

Figure 21D:
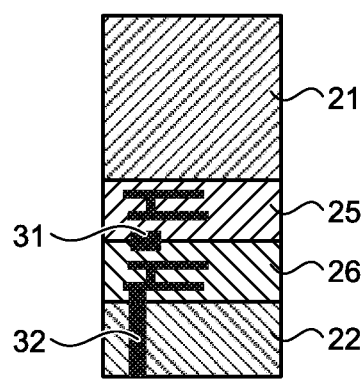
FIG. 21D is a schematic diagram illustrating a cross section of the imaging element at a manufacturing step in FIG. 20.

Subsequently, the semiconductor manufacturing apparatus forms a TSV in the ADC wafer (Step S204). Specifically, as illustrated in FIG. 21D, the semiconductor manufacturing apparatus forms, in the second chip 22, the TSV 32 connecting to the second multi-layered wiring layer 26.

Figure 21E:
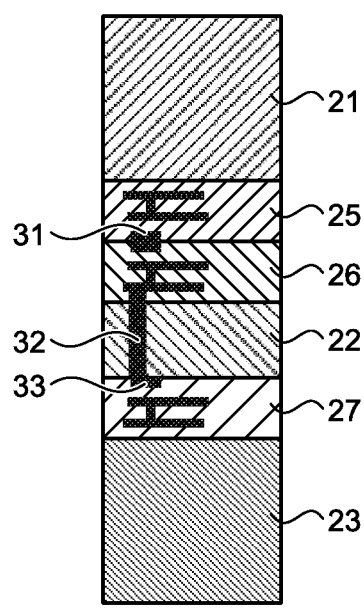
FIG. 21E is a schematic diagram illustrating a cross section of the imaging element at a manufacturing step in FIG. 20.

Thereafter, the semiconductor manufacturing apparatus layers and connects together the ADC wafer and the IF wafer (Step S205). Specifically, as illustrated in FIG. 21E, the third multi-layered wiring layer 27 on the third chip 23 and the electrode 33, which has been formed on the back surface of the second chip 22 and connects to the TSV 32, are connected to each other via hybrid bonding, a bump, or the like.

Figure 21F:
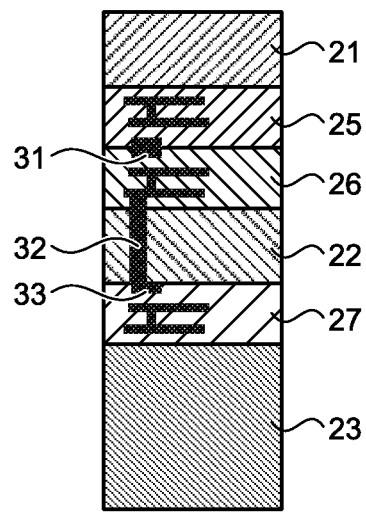
FIG. 21F is a schematic diagram illustrating a cross section of the imaging element at a manufacturing step in FIG. 20.

Subsequently, the semiconductor manufacturing apparatus performs thinning of the CIS wafer (Step S206). Specifically, as illustrated in FIG. 21F, the semiconductor manufacturing apparatus performs thinning of the first chip 21.

Figure 21G:
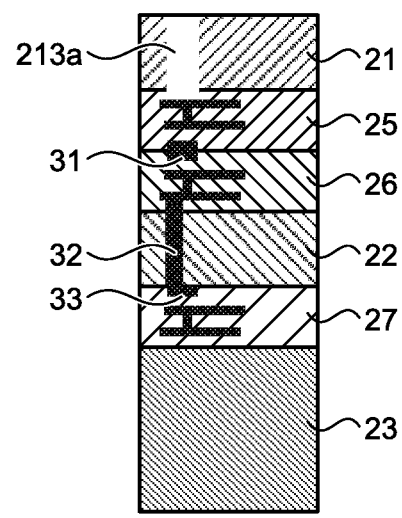
FIG. 21G is a schematic diagram illustrating a cross section of the imaging element at a manufacturing step in FIG. 20.

Thereafter, the semiconductor manufacturing apparatus opens a probing pad in the CIS wafer (Step S207). As illustrated in FIG. 21G, by performing etching processing on the Si substrate and insulating layer at the connecting portion 213 (the connected area) on the first chip 21 so as to expose, as a pad, a part of the first multi-layered wiring layer 25 on the first chip 21, the semiconductor manufacturing apparatus forms the probing pad 213a.

Subsequently, the semiconductor manufacturing apparatus forms an on-chip filter (OCF), such as a color filter or a micro-lens, on the CIS wafer (Step S208).

Thereafter, an inspection apparatus, which is not illustrated in the drawings, inspects the layered wafers (Step S209). Specifically, the inspection apparatus performs image inspection on the layered wafers by probing the probing pad 213a with an inspection probe.

Figure 21H:
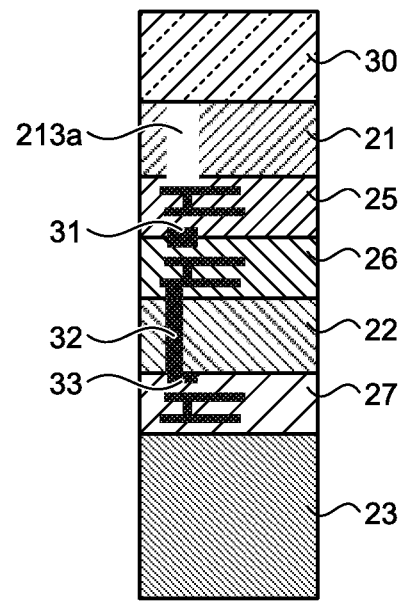
FIG. 21H is a schematic diagram illustrating a cross section of the imaging element at a manufacturing step in FIG. 20.

Subsequently, the semiconductor manufacturing apparatus bonds a cover glass to the CIS wafer (Step S210). Specifically, as illustrated in FIG. 21H, the semiconductor manufacturing apparatus bonds the cover glass 30 to the first chip 21.

Figure 21I:
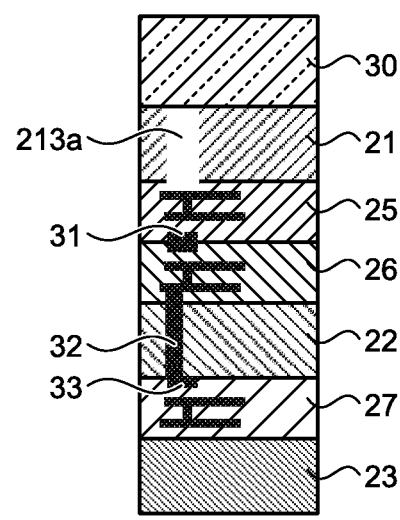
FIG. 21I is a schematic diagram illustrating a cross section of the imaging element at a manufacturing step in FIG. 20.

Thereafter, the semiconductor manufacturing apparatus performs thinning of the IF wafer (Step S211). Specifically, as illustrated in FIG. 21I, the semiconductor manufacturing apparatus performs thinning of the third chip 23.

Figure 21J:
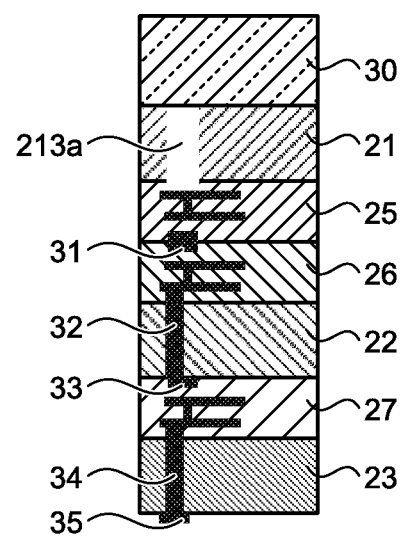
FIG. 21J is a schematic diagram illustrating a cross section of the imaging element at a manufacturing step in FIG. 20.

Subsequently, the semiconductor manufacturing apparatus forms a TSV in the IF wafer (Step S212), and forms an electrode on the back surface of the IF wafer (Step S213). Specifically, as illustrated in FIG. 21J, after forming the TSV 34 in the third chip 23, the semiconductor manufacturing apparatus forms the electrode 35 for external connection, on the back surface of the third chip 23. The semiconductor manufacturing apparatus thus manufactures the imaging element 20f to be used in this fifth embodiment, and ends this processing.

According to the above described fifth embodiment of the disclosure, similarly to the above described first embodiment, downsizing of the imaging element 20f is able to be realized.

First Modified Example of Fifth Embodiment

Next, a first modified example of the fifth embodiment of the disclosure will be described. A manufacturing method for the imaging element 20f according to this first modified example of the fifth embodiment is different from the above described manufacturing method for the imaging element 20f according to the fifth embodiment. Hereinafter, the manufacturing method for the imaging element 20f according to the first modified example of the fifth embodiment will be described. The same reference signs will be assigned to configurations that are the same as those of the above described endoscope system 1 according to the first embodiment.

Manufacturing Method for Imaging Element

FIG. 22 is a flow chart illustrating an outline of the manufacturing method for the imaging element 20f according to the first modified example of the fifth embodiment. FIG. 23A to FIG. 23L are schematic diagrams illustrating cross sections of the imaging element 20f at the respective manufacturing steps in FIG. 22. Hereinafter, since the imaging element 20f is manufactured by use of a well-known semiconductor manufacturing apparatus, description of the configuration of the semiconductor manufacturing apparatus will be omitted.

In FIG. 22, Step S301 to Step S303 correspond respectively to above described Step S201 to Step S203 in FIG. 20.

Figure 23A:
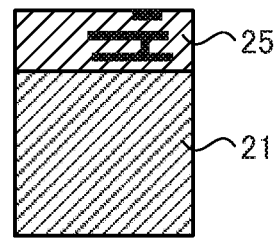
FIG. 23A is a schematic diagram illustrating a cross section of the imaging element at a manufacturing step in FIG. 22.
Figure 23B:
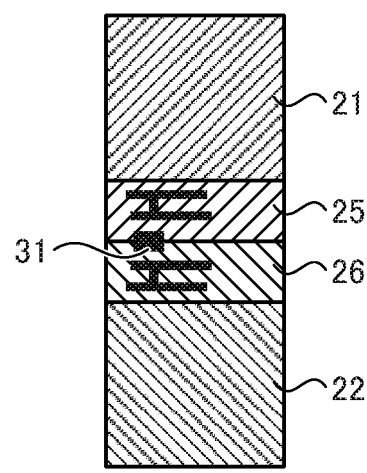
FIG. 23B is a schematic diagram illustrating a cross section of the imaging element at a manufacturing step in FIG. 22.
Figure 23C:
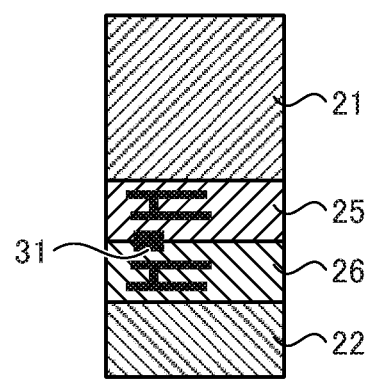
FIG. 23C is a schematic diagram illustrating a cross section of the imaging element at a manufacturing step in FIG. 22.
Figure 23D:
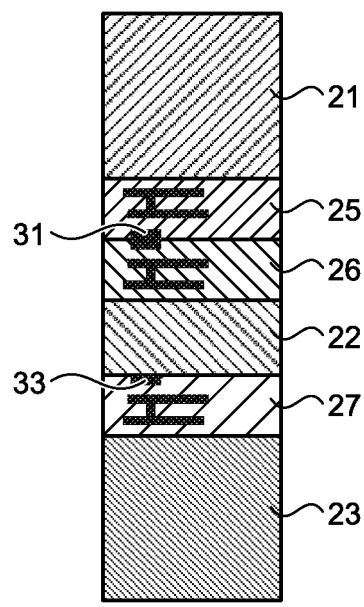
FIG. 23D is a schematic diagram illustrating a cross section of the imaging element at a manufacturing step in FIG. 22.

At Step S304, the semiconductor manufacturing apparatus layers and connects together the ADC wafer and the IF wafer. Specifically, as illustrated in FIG. 23D, the semiconductor manufacturing apparatus layers and connects the third multi-layered wiring layer 27 on the third chip 23 over and to the insulating film formed on the thinned surface of the second chip 22.

Figure 23E:
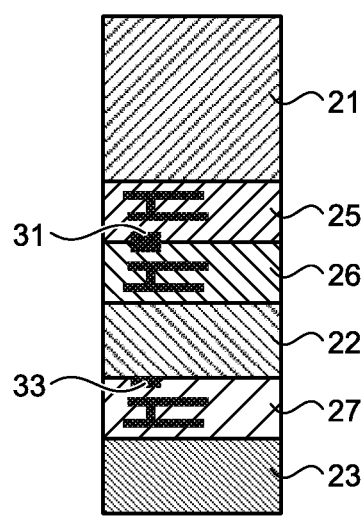
FIG. 23E is a schematic diagram illustrating a cross section of the imaging element at a manufacturing step in FIG. 22.

Subsequently, the semiconductor manufacturing apparatus performs thinning of the IF wafer (Step S305). Specifically, as illustrated in FIG. 23E, the semiconductor manufacturing apparatus performs thinning of the third chip 23.

Figure 23F:
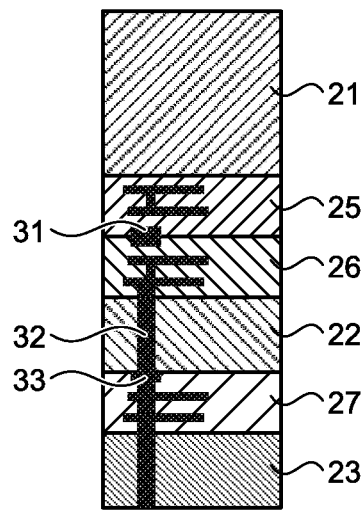
FIG. 23F is a schematic diagram illustrating a cross section of the imaging element at a manufacturing step in FIG. 22.

Thereafter, the semiconductor manufacturing apparatus forms a TSV in the ADC wafer and the IF wafer (Step S306). Specifically, as illustrated in FIG. 23F, the semiconductor manufacturing apparatus forms the TSV 32 in each of the second chip 22 and the third chip 23, and connects together the second multi-layered wiring layer 26 on the second chip 22 and the third multi-layered wiring layer 27 on the third chip 23.

Figure 23G:
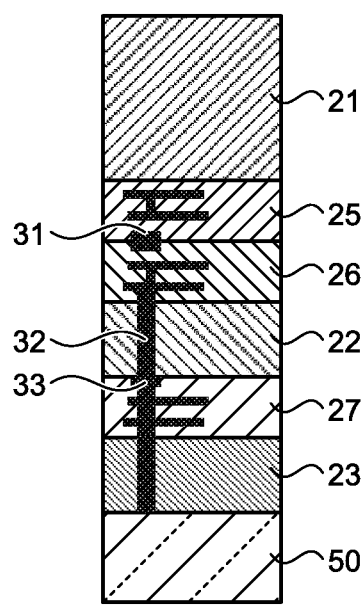
FIG. 23G is a schematic diagram illustrating a cross section of the imaging element at a manufacturing step in FIG. 22.
Figure 23H:
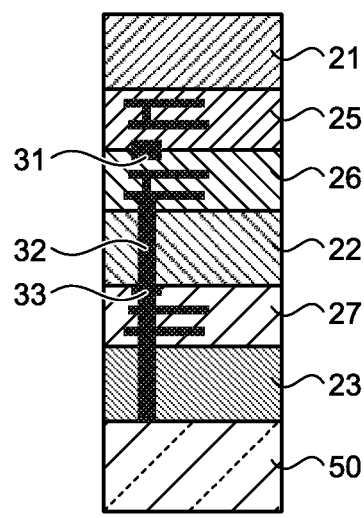
FIG. 23H is a schematic diagram illustrating a cross section of the imaging element at a manufacturing step in FIG. 22.
Figure 23I:
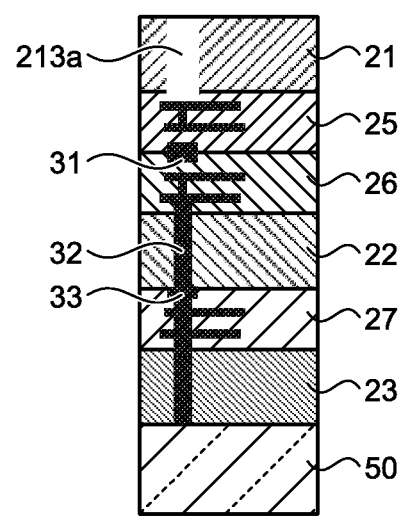
FIG. 23I is a schematic diagram illustrating a cross section of the imaging element at a manufacturing step in FIG. 22.
Figure 23J:
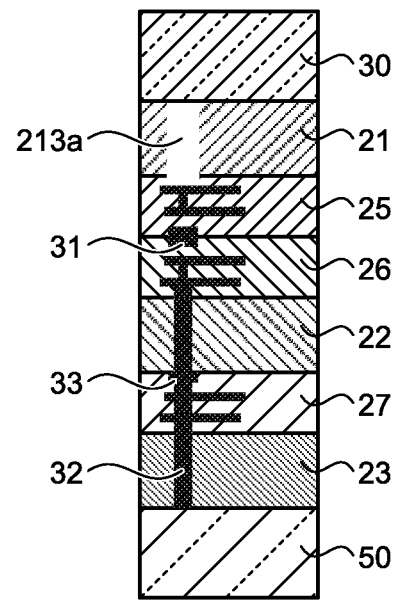
FIG. 23J is a schematic diagram illustrating a cross section of the imaging element at a manufacturing step in FIG. 22.

Subsequently, the semiconductor manufacturing apparatus connects a support wafer to the IF wafer (Step S307). Specifically, as illustrated in FIG. 23G, the semiconductor manufacturing apparatus temporarily connects a support wafer 50 to the back surface of the third chip 23.

Step S308 to Step S312 correspond respectively to above described Step S206 to Step S210 in FIG. 20.

Figure 23K:
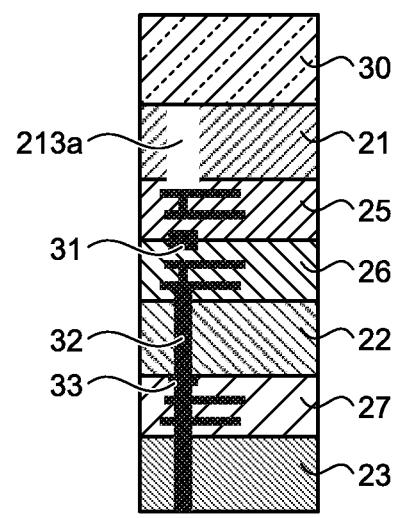
FIG. 23K is a schematic diagram illustrating a cross section of the imaging element at a manufacturing step in FIG. 22.

At Step S313, the semiconductor manufacturing apparatus peels off the support wafer. Specifically, as illustrated in FIG. 23K, the semiconductor manufacturing apparatus peels off the support wafer 50 from the back surface of the third chip 23.

Figure 23L:
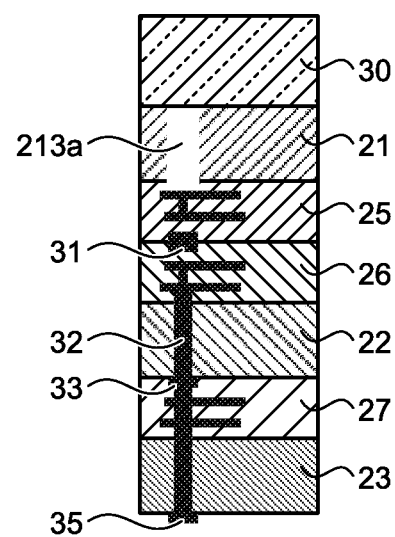
FIG. 23L is a schematic diagram illustrating a cross section of the imaging element at a manufacturing step in FIG. 22.

Subsequently, the semiconductor manufacturing apparatus forms an electrode on the back surface of the IF wafer (Step S314). Specifically, as illustrated in FIG. 23L, the semiconductor manufacturing apparatus forms the electrode 35 on the back surface of the third chip 23. The semiconductor manufacturing apparatus thus manufactures the imaging element 20f to be used in this first modified example of the fifth embodiment, and ends this processing.

The method where the thinning of the IF wafer (Step S305) and the TSV formation in the IF wafer (Step S306) are performed before the thinning of the CIS wafer (Step S308) has been described as an example, but the thinning of the CIS wafer (Step S308), the opening of the probing pad in the CIS wafer (Step S309), the formation of the on-chip filter (OCF) on the CIS wafer (Step S310), the inspection of the layered wafers (Step S311), and the bonding of the cover glass to the CIS wafer (Step S312) may be performed after electric connection between the ADC wafer and the IF wafer via the TSV 32 is performed before the thinning of the IF wafer (Step S305) and the TSV formation in the IF wafer (Step S306). In this case, since the capacitative wafer before the thinning processing functions as a support wafer in the thinning of the CIS wafer, steps for temporary connection and peeling of a support wafer are not separately needed, and the process is thus able to be simplified.

According to the above described first modified example of the fifth embodiment of the disclosure, similarly to the above described first embodiment, the imaging element 20f is able to be downsized.

Second Modified Example of Fifth Embodiment

Next, a second modified example of the fifth embodiment of the disclosure will be described. A configuration of an imaging element according to this second modified example of the fifth embodiment is different from the above described configuration of the imaging element 20f according to the fifth embodiment. Specifically, the above described imaging element 20f according to the fifth embodiment includes the probing pad 213a formed in the connecting portion 213 of the first chip 21, but the imaging element according to this second modified example of the fifth embodiment includes a probing pad, which is an electrode, formed on the back surface of the third chip 23. Hereinafter, after description of the configuration of the imaging element according to the second modified example of the fifth embodiment, a manufacturing method for the imaging element according to the second modified example of the fifth embodiment will be described. The same reference signs will be assigned to configurations that are the same as those of the above described endoscope system 1 according to the first embodiment, and description thereof will be omitted.

Configuration of Imaging Element

Figure 24:
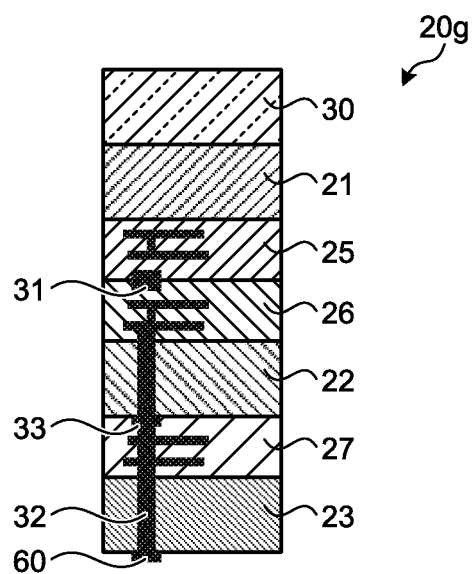
FIG. 24 is a schematic diagram illustrating a cross section of an imaging element according to a second modified example of the fifth embodiment of the disclosure.

FIG. 24 is a schematic diagram illustrating a cross section of the imaging element according to the second modified example of the fifth embodiment. An imaging element 20g illustrated in FIG. 24 includes a probing pad 60, which is an electrode, formed on the back surface of the third chip 23.

Manufacturing Method for Imaging Element

Figure 25:
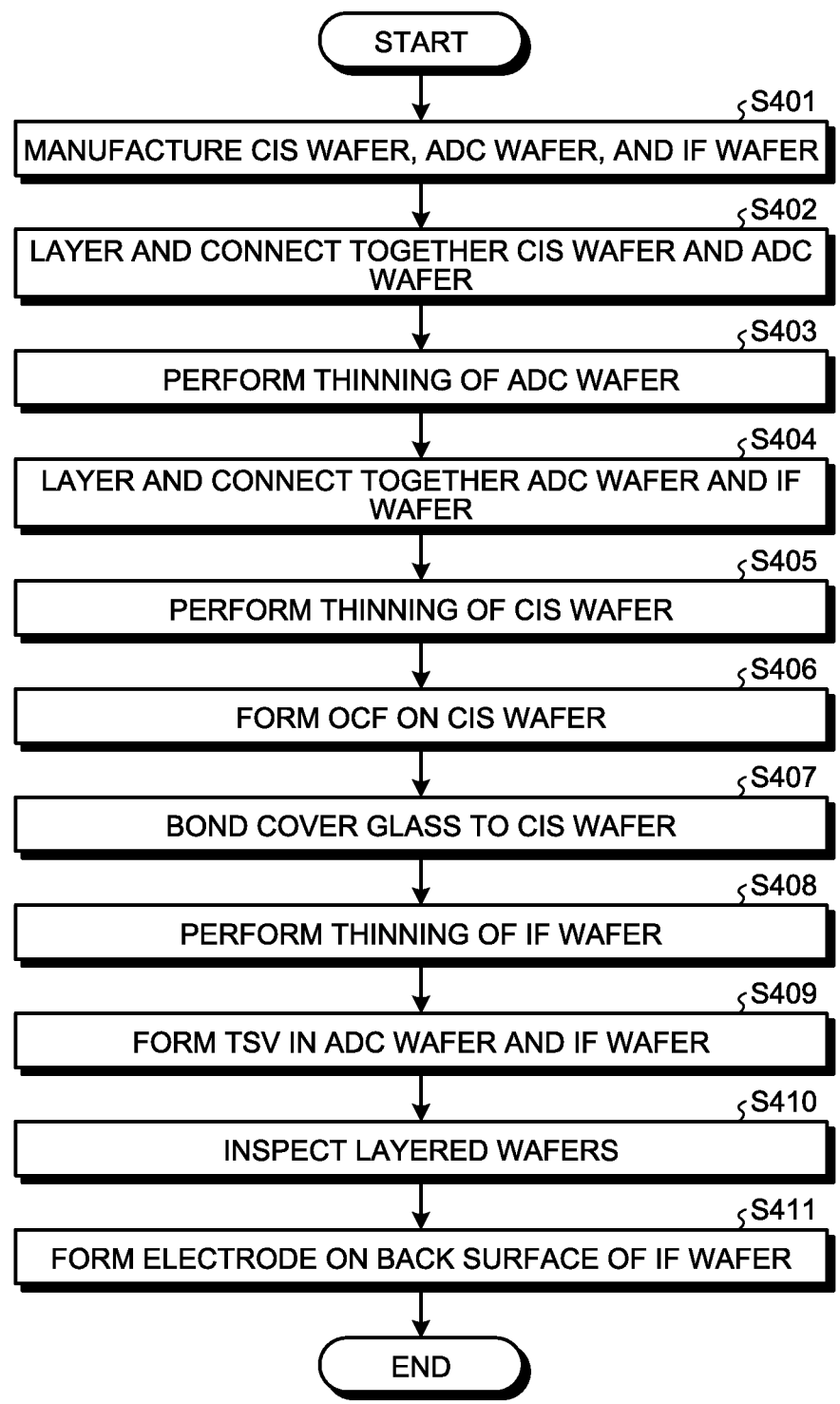
FIG. 25 is a flow chart illustrating an outline of a manufacturing method for the imaging element according to the second modified example of the fifth embodiment of the disclosure.

Next, the manufacturing method for the imaging element 20g according to the second modified example of the fifth embodiment will be described. FIG. 25 is a flow chart illustrating an outline of the manufacturing method for the imaging element 20g according to the second modified example of the fifth embodiment. FIG. 26A to FIG. 26I are schematic diagrams illustrating cross sections of the imaging element 20g at the respective manufacturing steps in FIG. 25. Hereinafter, since the imaging element 20g is manufactured by use of a well-known semiconductor manufacturing apparatus, description of the configuration of the semiconductor manufacturing apparatus will be omitted.

In FIG. 25, Step S401 to Step S403 respectively correspond to above described Step S201 to Step S203 in FIG. 20.

Figure 26A:
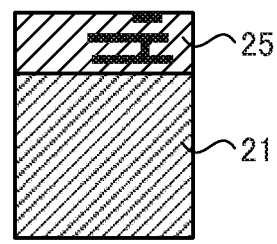
FIG. 26A is a schematic diagram illustrating a cross section of the imaging element at a manufacturing step in FIG. 25.
Figure 26B:
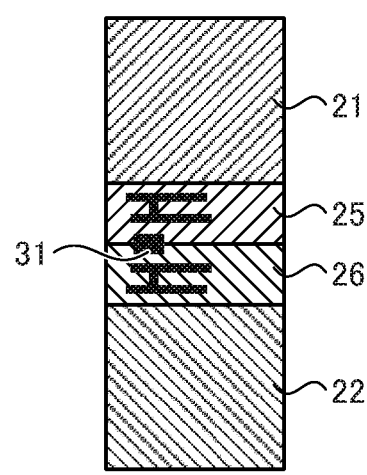
FIG. 26B is a schematic diagram illustrating a cross section of the imaging element at a manufacturing step in FIG. 25.
Figure 26C:
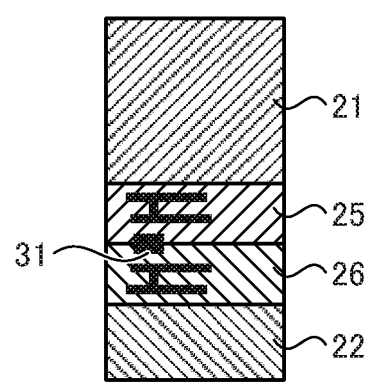
FIG. 26C is a schematic diagram illustrating a cross section of the imaging element at a manufacturing step in FIG. 25.
Figure 26D:
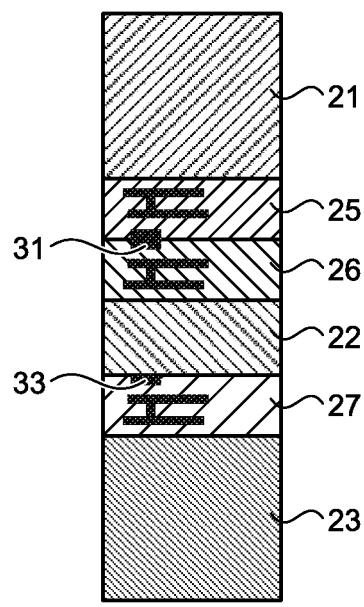
FIG. 26D is a schematic diagram illustrating a cross section of the imaging element at a manufacturing step in FIG. 25.

At Step S404, the semiconductor manufacturing apparatus layers and connects together the ADC wafer and the IF wafer. Specifically, as illustrated in FIG. 26D, the third multi-layered wiring layer 27 on the third chip 23 and the thinned surface of the second chip 22 are connected to each other by direct bonding or the like via the insulating films.

Figure 26E:
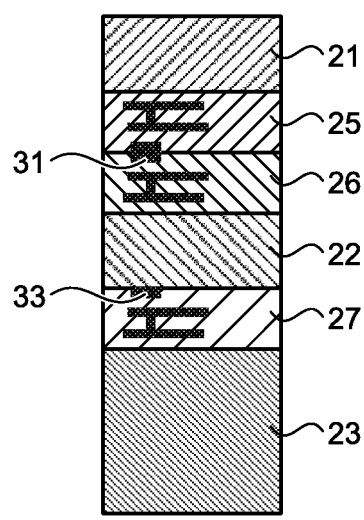
FIG. 26E is a schematic diagram illustrating a cross section of the imaging element at a manufacturing step in FIG. 25.

Subsequently, the semiconductor manufacturing apparatus performs thinning of the CIS wafer (Step S405). Specifically, as illustrated in FIG. 26E, the semiconductor manufacturing apparatus performs thinning of the first chip 21.

Thereafter, the semiconductor manufacturing apparatus forms an on-chip filter (OCF), such as a color filter or a micro-lens, on the CIS wafer (Step S406).

Figure 26F:
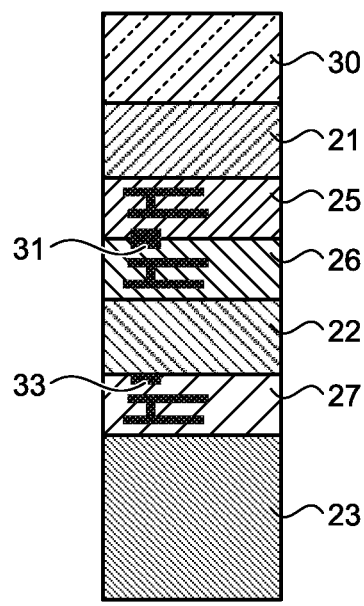
FIG. 26F is a schematic diagram illustrating a cross section of the imaging element at a manufacturing step in FIG. 25.

Subsequently, the semiconductor manufacturing apparatus bonds a cover glass to the CIS wafer (Step S407). Specifically, as illustrated in FIG. 26F, the semiconductor manufacturing apparatus bonds the cover glass 30 (the cover glass wafer) to the first chip 21.

Figure 26G:
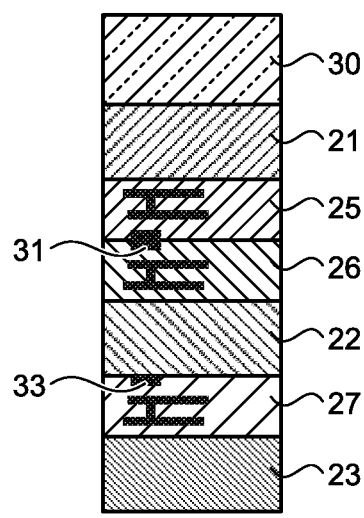
FIG. 26G is a schematic diagram illustrating a cross section of the imaging element at a manufacturing step in FIG. 25.

Thereafter, the semiconductor manufacturing apparatus performs thinning of the IF wafer (Step S408). Specifically, as illustrated in FIG. 26G, the semiconductor manufacturing apparatus performs thinning of the third chip 23.

Figure 26H:
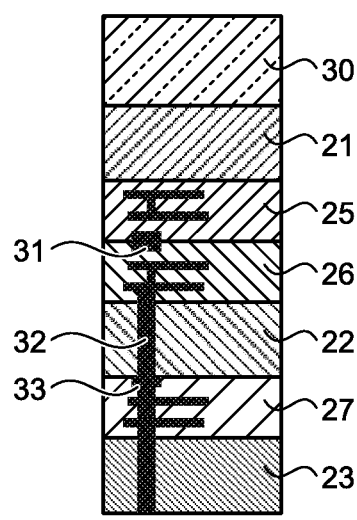
FIG. 26H is a schematic diagram illustrating a cross section of the imaging element at a manufacturing step in FIG. 25.

Subsequently, the semiconductor manufacturing apparatus forms a TSV in the ADC wafer and the IF wafer (Step S409). Specifically, as illustrated in FIG. 26H, the semiconductor manufacturing apparatus forms the TSV 32 in each of the second chip 22 and the third chip 23, and connects the second multi-layered wiring layer 26 on the second chip 22 and the third multi-layered wiring layer 27 on the third chip 23 to each other. Thereby, the back surface wiring connected to the TSV 32 functions as a probing pad.

Thereafter, an inspection apparatus, which is not illustrated in the drawings, inspects the layered wafers (Step S410). Specifically, as illustrated in FIG. 26H, the inspection apparatus inspects the imaging element 20g by causing an inspection probe to contact the back surface wiring connected to the TSV 32, the back surface wiring serving as the probing pad.

Figure 26I:
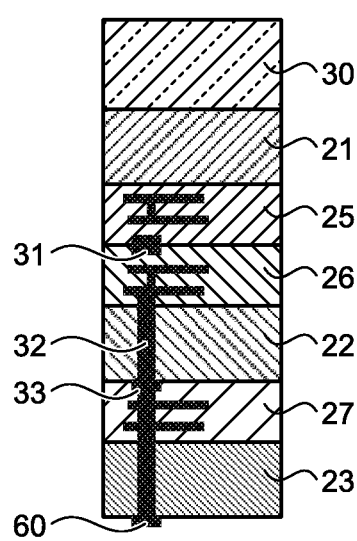
FIG. 26I is a schematic diagram illustrating a cross section of the imaging element at a manufacturing step in FIG. 25.

Subsequently, the semiconductor manufacturing apparatus forms an electrode on the back surface of the IF wafer (Step S411). Specifically, as illustrated in FIG. 26I, the semiconductor manufacturing apparatus forms the probing pad 60, which is an electrode, at a position where the TSV 32 has been formed in the third chip 23. The semiconductor manufacturing apparatus thus manufactures the imaging element 20g to be used in this second modified example of the fifth embodiment, and ends this processing.

According to the above described second modified example of the fifth embodiment of the disclosure, similarly to the first embodiment, downsizing of the imaging element 20g is able to be realized.

Third Modified Example of Fifth Embodiment

Next, a third modified example of the fifth embodiment of the disclosure will be described. A configuration of an imaging element according to this third modified example of the fifth embodiment is different from the above described configuration of the imaging element 20f according to the fifth embodiment. Hereinafter, the configuration of the imaging element according to the third modified example of the fifth embodiment will be described. The same reference signs will be assigned to configurations that are the same as those of the above described endoscope system 1 according to the first embodiment, and description thereof will be omitted.

Configuration of Imaging Element

Figure 27A:
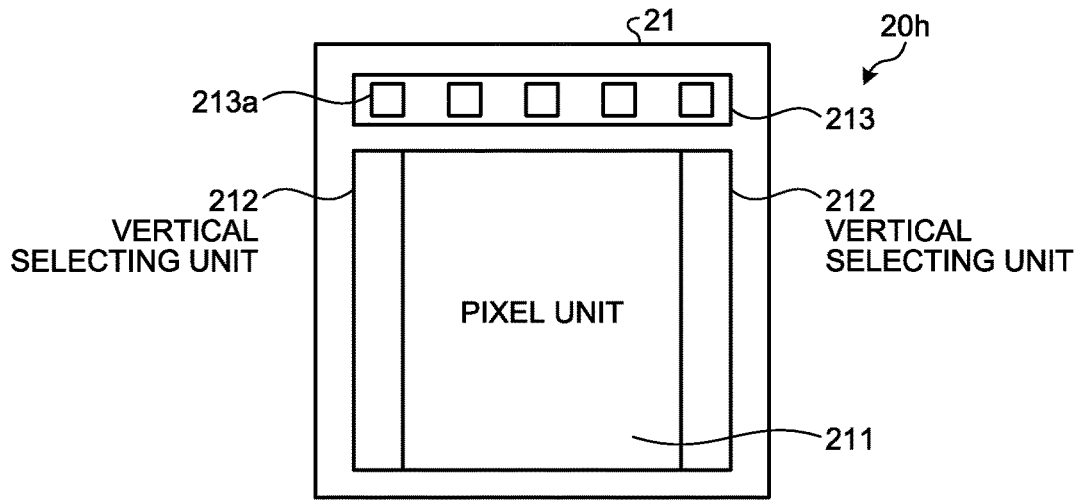
FIG. 27A is a plan view of a first chip of an imaging element according to a third modified example of the fifth embodiment of the disclosure.
Figure 27B:
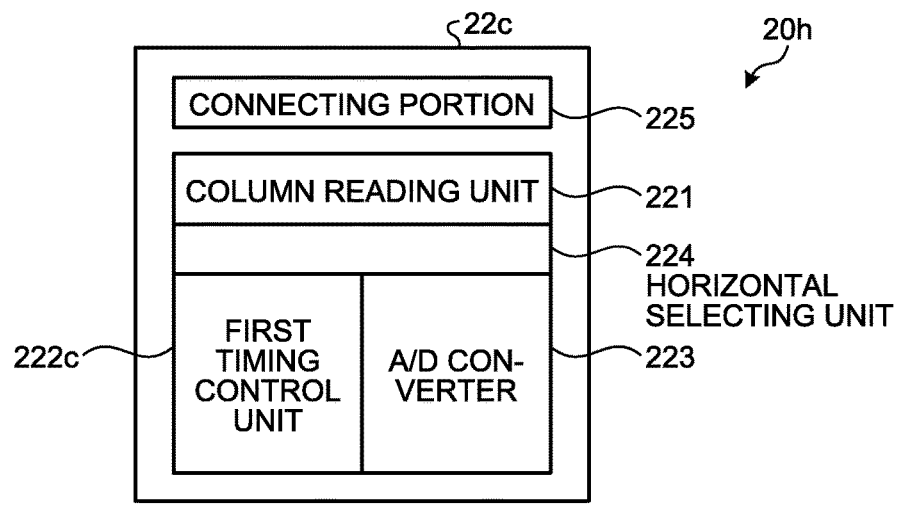
FIG. 27B is a plan view of a second chip of the imaging element according to the third modified example of the fifth embodiment of the disclosure.
Figure 27C:
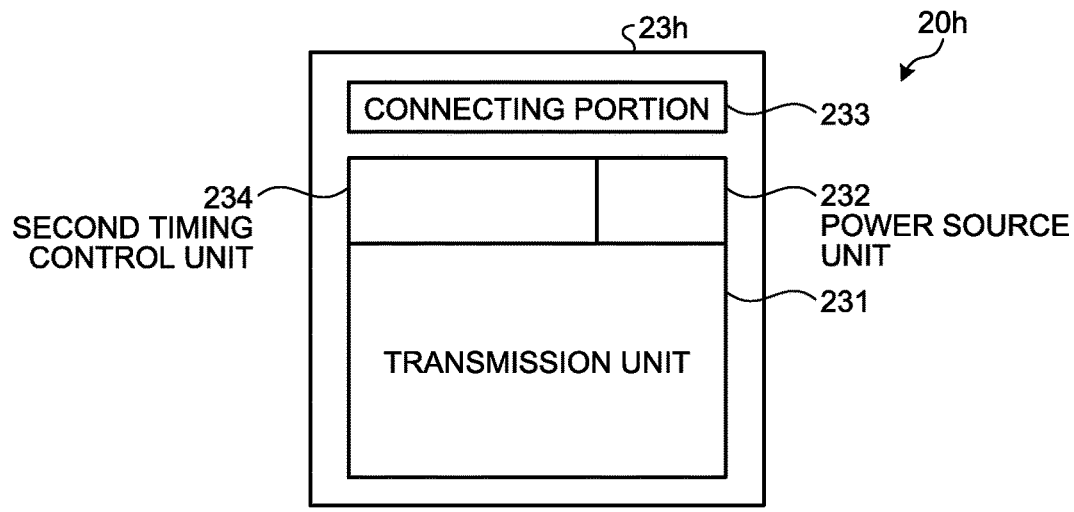
FIG. 27C is a plan view of a third chip of the imaging element according to the third modified example of the fifth embodiment of the disclosure.

FIG. 27A is a plan view of a first chip of the imaging element according to the third modified example of the fifth embodiment. FIG. 27B is a plan view of a second chip of the imaging element according to the third modified example of the fifth embodiment. FIG. 27C is a plan view of a third chip of the imaging element according to the third modified example of the fifth embodiment.

As illustrated in FIG. 27A to FIG. 27C, an imaging element 20h includes the first chip 21, the second chip 22c, and a third chip 23h.

The third chip 23h includes: the transmission unit 231; the power source unit 232; a second timing control unit 234 (a second timing control circuit) that generates a control signal for driving the vertical selecting unit 212; and a connecting portion 233c.

According to the above described third modified example of the fifth embodiment of the disclosure, since the drive signal of the vertical selecting unit 212 is a low-speed signal that has a long pulse width as compared to a period of the reference clock signal (for example, that switches between high and low in units of horizontal scanning periods), by the provision of the second timing control unit 234 in the third chip 23h, the sensor size of the imaging element 20h is able to be optimized without further inclusion of a circuit that adjusts timing variation caused by signal transmission among the chips.

According to the third modified example of the fifth embodiment of the disclosure, the first timing control unit 222c is provided on the second chip 22c, and the second timing control unit 234 is provided on the third chip 23h, but the first timing control unit 222c may be provided on the third chip 23h, and the second timing control unit 234 may be provided on the second chip 22c.

Other Embodiments

According to the above described embodiments, the endoscopes are those that are inserted in subjects, but the embodiments are also applicable to a capsule type endoscope or an imaging device for imaging a subject.

In the description of the timing charts and the flow charts in this specification, the context of the processing among the respective steps is disclosed by use of expressions such as "firstly", "thereafter", and "subsequently", but sequences of the processing necessary for implementation of the disclosure are not uniquely defined by these expressions. That is, the sequences of the processing in the timing charts and flow charts described in this specification may be modified as far as no contradiction arises from the modification.

Further, the above described "section, module, or unit" may be interpreted as "a means", "a circuit", or the like. For example, a control unit may be interpreted as a control means or a control circuit.

Accordingly, the disclosure may include various embodiments not described herein, and various design changes and the like within the scope of the technical ideas specified by the scope of the claims may be made.

The disclosure has an effect of enabling further downsizing to be realized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging element, comprising:
    a pixel chip where a pixel unit and a vertical selecting unit are arranged, the pixel unit including plural pixels that are arranged in a two-dimensional matrix, the pixels being configured to generate and output imaging signals according to quantity of received light, the vertical selecting unit being configured to sequentially select the pixel unit in row units and read out the imaging signals;
    a transmission chip where at least a power source unit and a transmission unit configured to transmit the imaging signals to a transmission cable are arranged;
    plural capacitative chips, each capacitative chip having capacitance functioning as a bypass condenser for a power source in the power source unit; and
    plural connecting portions configured to electrically connect the pixel chip, the transmission chip, and the capacitative chip respectively to another chip, wherein
    the transmission chip is layered and connected, along a direction orthogonal to a light receiving surface of the pixel unit, at a back surface side of the pixel chip relative to a light entering surface of the pixel chip, by the connecting portions,
    the capacitative chips are layered and connected, along the direction orthogonal to the light receiving surface of the pixel unit, at a back surface side of the transmission chip relative to a surface of the transmission chip, the surface being where the pixel chip has been layered, and
    the connecting portions are arranged so as to overlap one another as viewed in the direction orthogonal to the light receiving surface of the pixel unit.

2. The imaging element according to claim 1, further comprising:
    a functional chip that are layered and connected along the direction orthogonal to the light receiving surface of the pixel unit and where plural function executing units configured to execute predetermined functions are arranged, wherein the connecting portions are configured to electrically connect the pixel chip, the transmission chip, the capacitative chip, and the functional chip respectively to another chip.

3. The imaging element according to claim 2, wherein the plural function executing units include:
- a reading unit configured to sequentially select predetermined pixels from the plural pixels and read out the imaging signals output from the selected pixels;
- a timing control unit configured to control timing for the reading unit to read out the imaging signals output from the selected pixels; and
- an A/D converter configured to performs A/D conversion on analog imaging signals output from the pixel chip.

4. The imaging element according to claim 1, further comprising a probing pad to be contacted with an inspection probe, such that the probing pad overlaps the connecting portions.

5. The imaging element according to claim 4, wherein the probing pad is formed at the pixel chip so as to overlap the connecting portions as viewed from a light receiving surface side of the pixel unit.

6. The imaging element according to claim 5, further comprising a cover glass that is layered over a surface of the pixel chip, along the direction orthogonal to the light receiving surface of the pixel unit, the surface including a position of the probing pad.

7. The imaging element according to claim 4, wherein the probing pad is formed at a back surface side of the pixel unit relative to the light receiving surface of the pixel unit so as to overlap the connecting portions as viewed from the light receiving surface side of the pixel unit.

8. The imaging element according to claim 3, wherein the transmission unit includes:
- a driver configured to transmit the imaging signals to the transmission cable by a differential method; and
- a multiplying unit configured to output a high-speed clock signal resulting from multiplication of a clock signal input from outside according to the number of bits of the A/D converter, and the A/D converter includes:
- a converter configured to convert the imaging signal read out by the reading unit, into a multi-bit digital signal; and
- a serializer configured to convert, based on the high-speed clock signal output by the multiplying unit, a parallel digital signal that is the multi-bit digital signal into a serial digital signal, and transmit the serial digital signal to the transmission cable via the driver.

9. The imaging element according to claim 3, wherein the timing control unit includes:
- a first timing control unit configured to generate a control signal for driving the vertical selecting unit configured to read out the imaging signals from the pixel unit to a vertical transfer line; and
- a second timing control unit configured to generate a control signal for driving another function executing unit, the first timing control unit is arranged at the third chip, and the second timing control unit is arranged at the second chip.

10. An endoscope, comprising:
the imaging element according to claim 1, at a distal end of an insertion unit of the endoscope, the insertion unit being insertable in a subject.

11. An endoscope system, comprising:
the endoscope according to claim 10; and
an image processing apparatus configured to convert the imaging signals into image signals.

* * * * *